US012754055B2

(12) United States Patent
Gaskin et al.

(10) Patent No.: US 12,754,055 B2
(45) Date of Patent: Oct. 6, 2026

(54) FLUID MEASURING RESERVOIR FOR BREAST PUMPS

(71) Applicant: WILLOW INNOVATIONS, INC., Mountain View, CA (US)

(72) Inventors: Nathaniel Gaskin, Palo Alto, CA (US); Jeffery B. Alvarez, Redwood City, CA (US); Janica B. Alvarez, Redwood City, CA (US)

(73) Assignee: Willow Innovations, Inc., Mountain View, CA (US)

( * ) Notice: Subject to any disclaimer, the term of this patent is extended or adjusted under 35 U.S.C. 154(b) by 540 days.

(21) Appl. No.: 16/808,718

(22) Filed: Mar. 4, 2020

(65) Prior Publication Data

US 2020/0197584 A1 Jun. 25, 2020

Related U.S. Application Data

(63) Continuation of application No. 15/094,704, filed on Apr. 8, 2016, now Pat. No. 10,617,805.

(Continued)

(51) Int. Cl.

| | |
|---|---|
| ***G01F 23/26*** | (2022.01) |
| ***A61J 9/00*** | (2006.01) |
| ***A61M 1/06*** | (2006.01) |
| ***G16H 40/63*** | (2018.01) |
| ***H04L 67/1095*** | (2022.01) |

(Continued)

(52) U.S. Cl.

CPC ................ *G01F 23/26* (2013.01); *A61J 9/00* (2013.01); *A61M 1/06* (2013.01); *A61M 1/062* (2014.02); *G16H 40/63* (2018.01); *H04L 67/1095* (2013.01); *H04L 67/12* (2013.01); *H04W 4/80* (2018.02); *A61J 2200/50* (2013.01);

(Continued)

(58) Field of Classification Search

CPC .................... A61M 1/06; A61M 1/062; A61M 2205/3389; A61M 2205/50; G16H 40/63; H04W 4/80; A61J 9/00; H04L 67/1095; H04L 67/12

See application file for complete search history.

(56) References Cited

U.S. PATENT DOCUMENTS

| | | | |
|---|---|---|---|
| 3,696,675 | A | 10/1972 | Gilmour |
| 4,263,912 | A | 4/1981 | Adams |

(Continued)

FOREIGN PATENT DOCUMENTS

| | | |
|---|---|---|
| CN | 201840674 | 5/2011 |
| CN | 104382742 | 3/2015 |

(Continued)

OTHER PUBLICATIONS

International search report and written opinion dated Jul. 7, 2016 for PCT/US2016/026827.

*Primary Examiner* — Lauren P Farrar

(57) ABSTRACT

Systems, methods, and apparatus are provided for containing and measuring a fluid in a reservoir. A sensing reservoir comprises a reservoir comprising an opening and a wall, the opening configured to allow passage of the fluid in and out of the reservoir, and the wall defining a chamber configured to contain the fluid. The sensing reservoir further comprises a fluid sensing unit coupled to the sensing reservoir, the fluid sensing unit configured to generate measurement data indicative of a volume of the fluid contained in the reservoir.

21 Claims, 20 Drawing Sheets

Related U.S. Application Data

(60) Provisional application No. 62/144,857, filed on Apr. 8, 2015.

(51) Int. Cl.
*H04L 67/12* (2022.01)
*H04W 4/80* (2018.01)

(52) U.S. Cl.
CPC ... *A61J 2200/76* (2013.01); *A61M 2205/3389* (2013.01); *A61M 2205/50* (2013.01)

(56) References Cited

U.S. PATENT DOCUMENTS 5,423,781 A 6/1995 Alexander et al.
5,885,246 A 3/1999 Ford
6,125,696 A 10/2000 Hannan et al.
6,164,132 A 12/2000 Matulek
6,490,920 B1 12/2002 Netzer
6,616,037 B2 9/2003 Grimm et al.
6,652,484 B1 11/2003 Hunckler et al.
6,673,036 B1 1/2004 Britto
6,749,582 B2 6/2004 Britto et al.
6,840,918 B1 1/2005 Britto et al.
6,887,210 B2 5/2005 Quay
7,029,454 B2 4/2006 Watanabe
7,118,709 B2 10/2006 Treptow
7,600,423 B1 10/2009 Fluhler et al.
7,662,127 B2 2/2010 Silver et al.
7,758,540 B2 7/2010 Yamashita et al.
7,875,000 B2 1/2011 Krebs et al.
7,972,297 B2 7/2011 Bryan et al.
8,116,933 B2 2/2012 Underdal et al.
8,118,772 B2 2/2012 Dao et al.
8,164,454 B2 4/2012 Teller
8,216,179 B2 7/2012 Bosshard et al.
8,323,235 B2 12/2012 Bryan et al.
8,453,878 B2 6/2013 Palmquist
8,690,578 B1 * 4/2014 Nusbaum ................ G16Z 99/00 705/2
8,801,658 B2 8/2014 Horari et al.
8,813,551 B2 8/2014 Boiarski
8,827,947 B2 9/2014 Bosman et al.
8,876,760 B2 11/2014 Bosman et al.
9,033,953 B2 5/2015 Felber
2002/0032403 A1 3/2002 Savagle et al.
2005/0172712 A1 8/2005 Nyce
2005/0234370 A1 10/2005 Beal et al.
2006/0042376 A1 * 3/2006 Reusche ............. G01F 23/2962 73/304 C
2006/0072928 A1 4/2006 Young
2007/0125162 A1 6/2007 Ghazi et al.
2007/0277816 A1 12/2007 Morrison et al.
2009/0178479 A1 7/2009 Pagovich et al.
2010/0217148 A1 8/2010 Binder
2011/0084842 A1 4/2011 Tzidon et al.
2011/0087078 A1 4/2011 Zemel et al.
2011/0240136 A1 10/2011 Trottier
2011/0314907 A1 12/2011 Wiedekind-Klein
2012/0004637 A1 1/2012 Krulevitch et al.
2012/0097567 A1 4/2012 Zhao et al.
2012/0277737 A1 11/2012 Curley
2013/0096461 A1 4/2013 Sella
2013/0131588 A1 5/2013 Silver et al.
2013/0245548 A1 9/2013 Cook et al.
2013/0261539 A1 10/2013 King
2013/0310756 A1 * 11/2013 Whalley ................. A61M 5/31 604/189
2014/0095103 A1 * 4/2014 Temko ................. B67D 3/0051 702/128
2014/0121593 A1 5/2014 Felber et al.
2014/0142537 A1 * 5/2014 Gibson ............. A61M 5/16831 604/67
2014/0242213 A1 * 8/2014 McCarty ................. A23L 33/30 222/146.2
2014/0262918 A1 9/2014 Chu
2014/0263611 A1 * 9/2014 Bauer ................... A61M 1/062 604/74
2014/0276629 A1 9/2014 Bauer et al.
2014/0288466 A1 9/2014 Alvarez et al.
2014/0336615 A1 * 11/2014 Uram .................... A61M 5/142 604/67
2015/0027157 A1 1/2015 Chou et al.
2015/0038945 A1 2/2015 McCabe
2015/0047825 A1 2/2015 Strong
2015/0051458 A1 2/2015 Chen et al.
2015/0122688 A1 * 5/2015 Dias ..................... A47G 19/027 206/459.1
2015/0196247 A1 * 7/2015 Lau ......................... G01F 1/363 600/301
2015/0265753 A1 * 9/2015 Prentice .................. A61M 1/74 604/74
2015/0274329 A1 10/2015 Harp et al.
2015/0283311 A1 10/2015 Alvarez et al.
2015/0314053 A1 11/2015 Furrer et al.
2015/0328380 A1 11/2015 Furrer et al.
2016/0000980 A1 1/2016 Alvarez et al.
2016/0000981 A1 1/2016 Alvarez et al.
2016/0082165 A1 3/2016 Alvarez et al.
2016/0123876 A1 5/2016 Muldoon
2016/0138958 A1 * 5/2016 Truong ................... G01F 22/00 250/227.28
2016/0183602 A1 * 6/2016 Rider ...................... A61M 1/06 450/36
2017/0119970 A1 5/2017 Bammer et al.

FOREIGN PATENT DOCUMENTS

CN 204364469 6/2015
CN 105520838 4/2016
WO WO2013187763 12/2013
WO WO2017045902 3/2017

* cited by examiner

FLUID MEASURING RESERVOIR FOR BREAST PUMPS

CROSS-REFERENCE

The present application is a non-provisional of, and claims the benefit of U.S. Provisional Patent Application No. 62/144,857, filed on Apr. 8, 2015, and is a continuation of U.S. application Ser. No. 15/094,704, filed Apr. 8, 2016, the entire content of which is incorporated herein by reference.

This application is related to the following co-pending provisional and non-provisional patent applications: U.S. patent application Ser. No. 14/221,113, filed on Mar. 20, 2014, U.S. patent application Ser. No. 14/616,557, filed on Feb. 6, 2015, U.S. patent application Ser. No. 14/793,606, filed on Jul. 7, 2015, U.S. patent application Ser. No. 14/793,613, filed on Jul. 7, 2015, U.S. patent application Ser. No. 14/793,617, filed on Jul. 7, 2015, U.S. patent application Ser. No. 14/858,924, filed on Sep. 18, 2015, and U.S. Provisional Patent Application No. 62/144,854, filed on Apr. 8, 2015, the entire contents of which are incorporated herein by reference.

BACKGROUND OF THE INVENTION

1. Field of the Invention

The present invention generally relates to medical and pediatric nutrition devices and methods, and more particularly relates to devices and methods for expression and collection of human breast milk.

Breast pumps are commonly used to collect breast milk in order to allow mothers to continue breastfeeding while apart from their children. In order to understand their milk production and ensure that the production is maintained at a sufficient level, mothers often keep records of their pumping sessions manually, for example in journals or spreadsheets. Manual record keeping can be cumbersome and prone to inaccuracies or lapses in record-keeping.

It would be desirable to provide a way for mothers to automatically keep track of their milk production and the consumption of milk by their infants. It would be further desirable for the means to quantify breast milk production to be adaptable for use with various types of breast pumps. Automatic milk production quantification and inventory tracking via communication with mobile devices are further desirable for enhanced user convenience.

At least some of these objectives will be satisfied by the devices and methods disclosed below.

2. Description of the Background Art

The following US patents are related to expression and collection of human breast milk: U.S. Pat. Nos.: 6,673,036; 6,749,582; 6,840,918; 6,887,210; 7,875,000; 8,118,772; and 8,216,179.

SUMMARY OF THE INVENTION

The present invention generally relates to medical devices and methods, and more particularly relates to devices and methods for expression and collection of human breast milk.

Systems, methods, and apparatus are provided for containing and measuring a fluid in a reservoir. A sensing reservoir comprises a reservoir comprising an opening and a wall, the opening configured to allow passage of the fluid in and out of the reservoir, and the wall defining a chamber configured to contain the fluid. The sensing reservoir further comprises a fluid sensing unit coupled to the sensing reservoir, the fluid sensing unit configured to generate measurement data indicative of a volume of the fluid contained in the reservoir.

In one aspect, an apparatus for containing and measuring a fluid is provided. The apparatus comprises a reservoir and a fluid sensing unit coupled to the reservoir. The reservoir comprises an opening configured to allow passage of the fluid in and out of the reservoir, and a wall defining a chamber configured to contain the fluid. The fluid sensing unit may be configured to generate measurement data indicative of a volume of the fluid contained in the reservoir.

In some embodiments, the fluid sensing unit is coupled to the wall of the reservoir. The fluid sensing unit may be coupled to an exterior surface of the wall of the reservoir. The exterior surface of the wall of the reservoir may comprise a recessed region, wherein the fluid sensing unit may be received within the recessed region and coupled directly or indirectly to the exterior surface of the wall. The fluid sensing unit may be embedded in the wall of the reservoir adjacent an interior surface of the wall of the reservoir.

The apparatus may further comprise an insulating unit coupled to the reservoir. The insulating unit may be configured to cover the fluid sensing to provide one or more of electrical isolation or protection from physical damage of the fluid sensing unit. The insulating unit may comprise a material with high electrical resistance, such as one or more plastics or rubbers configured to provide electrical isolation of the fluid sensing unit. The insulating unit may be configured to provide an air gap between the insulating unit and fluid sensing unit. For example, the insulating unit may comprise an internal surface defining a cavity configured to receive a fluid sensor of the fluid sensing unit therein. The cavity may have a thickness greater than a thickness of the fluid sensor, thereby establishing an air gap between the insulting unit and the fluid sensor when the fluid sensor is disposed within the cavity.

The apparatus may further comprise a processing unit in communication with the fluid sensing unit, the processing unit configured to receive the measurement data from the fluid sensing unit. The processing unit may comprise a communication module configured to communicate with one or more of a computing device or a server. The processing unit may further comprise a memory configured to store the measurement data. The apparatus may further comprise a power source operatively coupled to one or more of the fluid sensing unit or the processing unit. The apparatus may further comprise a housing coupled to the wall of the reservoir, the housing configured to encase one or more of the fluid sensing unit, the processing unit, or the power source. The housing may be removably coupled to the reservoir.

In some embodiments, the fluid sensing unit comprises one or more capacitive sensors, wherein the one or more capacitive sensors may be in communication with a processing unit. The one or more capacitive sensors may be configured to measure a change in capacitance of the one or more capacitive sensors. The change in capacitance can be affected by the fluid in proximity to the one or more capacitive sensors, such that the measurement data generated by the one or more capacitive sensors can produce an indication of the volume of the fluid contained in the reservoir. The change in capacitance may comprise one or more of a change in self-capacitance between a capacitive sensor and a surrounding environment, or a change in a mutual capacitance between a first capacitive sensor of the one or more capacitive sensors and a second capacitive sensor of the one or more capacitive sensors.

Each of the one or more capacitive sensors may comprise one or more continuous sensing regions, each continuous sensing region extending continuously along a length of the reservoir. Alternatively or in combination, each of the one or more capacitive sensors may comprise an array of discrete sensing regions, the array of discrete sensing regions extending along a length of the reservoir. Each of the one or more capacitive sensors may comprise one or more sensing regions configured to increase in area from one end of the sensing region to the other end of the sensing region. For example, each discrete sensing region of the array of discrete sensing regions may comprise an area, wherein the area of a first discrete sensing region disposed adjacent a first end of the array is greater than the area of a second discrete region disposed adjacent a second end of the array opposite the first end.

In some embodiments, the fluid sensing unit comprises one or more base sensors coupled to one or more fluid sensors of the fluid sensing unit. The one or more base sensors may be configured to electrically isolate the one or more fluid sensors from sources of interference outside the reservoir.

The fluid sensing unit may comprise a plurality of fluid sensors distributed about the reservoir in a predetermined distribution. For example, the predetermined distribution may comprise an equal distribution about the periphery of the reservoir.

The apparatus may further comprise one or more reservoir sensors configured to measure one or more of a position, orientation, or motion of the apparatus. The one or more reservoir sensors may comprise one or more of an accelerometer and a gyroscope. The one or more reservoir sensors may be coupled to a processing unit of the apparatus, the processing unit in communication with the fluid sensing unit.

The apparatus may further comprise one or more proximity sensors. The one or more proximity sensors may be configured to detect presence of one or more proximity triggers disposed within a predetermined distance from the one or more proximity sensors. The one or more proximity triggers may be coupled to a component comprising a coupling mechanism to couple the component to the reservoir, such that the one or more proximity triggers can be placed within the predetermined distance when the component is coupled to the reservoir.

The component may comprise a pumping device, a feeding attachment, or a storage cap.

The one or more proximity sensors may comprise one or more assemblies of a light source and a light detector, and the one or more proximity triggers may comprise one or more reflective markers. The light source may be configured to emit light towards the one or more proximity triggers, the one or more reflective markers may be configured to reflect the light, and the light detector may be configured to detect the reflected light.

The one or more proximity sensors may comprise one or more Hall effect sensors, and the one or more proximity triggers may comprise one or more magnets. The one or more Hall effect sensors may be configured to detect an intensity of a magnetic field generated by the one or more magnets.

The one or more proximity sensors may comprise one or more reed switches, and the one or more proximity triggers may comprise one or more magnets. The one or more reed switches may be configured to electrically switch on or off in response to detection of a magnetic field generated by the one or more magnets.

The apparatus may further comprise a processing unit in communication with the fluid sensing unit and the one or more proximity sensors, wherein the processing unit is configured to identify a type of the component in response to measurement data generated by the one or more proximity sensors. The one or more proximity sensors may be configured to produce different readout values when components of different types are coupled to the reservoir. The processing unit may be configured to associate each component of a specific type with a specific readout value to identify the type of the component coupled to the reservoir. The components of different types may comprise proximity triggers configured to have different properties. The components of different types may comprise different numbers of proximity triggers. The one or more proximity sensors may comprise a plurality of proximity sensors disposed at different locations of the reservoir, and the processing unit may be configured to associate each component of a specific type with one or more of the plurality of proximity sensors disposed at one or more specific locations to identify the type of the component coupled to the reservoir.

The processing unit may be configured to switch between a standby state and a measurement state in response to measurement data generated by the one or more proximity sensors. The fluid sensing unit may operate in a low-power standby mode during the standby state. The fluid sensing unit may obtain the measurement data during the measurement state.

The processing unit may be configured to determine, in response to measurement data generated by the one or more proximity sensors, an analysis mode for analyzing the measurement data generated by the fluid sensing unit. The analysis mode may correspond to a filling state or a draining state of the reservoir.

The fluid sensing unit may be encased within an insulating unit coupled to the wall of the reservoir, and the one or more proximity sensors may be disposed within the insulating unit adjacent the fluid sensing unit and near the opening of the reservoir.

In another aspect, a system for containing and measuring a fluid is provided. The system comprises a sensing reservoir for containing and measuring a fluid, wherein the sensing reservoir may comprise a fluid sensing unit coupled to a reservoir. The fluid sensing unit may be configured to generate measurement data indicative of a volume of the fluid contained in the reservoir. The system further comprises a computing device in communication with the reservoir, the computing device configured to receive the measurement data.

In some embodiments, the sensing reservoir further comprises a communication module, and the computing device communicates with the sensing reservoir via the communication module. In some embodiments, the sensing reservoir further comprises one or more reservoir sensors configured to measure one or more of a position, orientation, or motion of the sensing reservoir.

The computing device may comprise a processing unit having instructions stored thereon for performing an analysis of the measurement data. The computing device may further comprise a user interface configured to display the measurement data to a user.

The system may further comprise a remote server in communication with the reservoir or the computing device.

The remote server may be configured to perform one or more of analysis and storage of the measurement data.

In another aspect, a method of measuring a fluid contained in a reservoir is provided. The method comprises providing a sensing reservoir for containing and measuring a fluid, wherein the sensing reservoir comprises a fluid sensing unit coupled to a reservoir. The method further comprises performing a system check to ensure that the sensing reservoir is functioning properly. The method further comprises generating measurement data using the fluid sensing unit, wherein the measurement data is indicative of a volume of the fluid contained in the reservoir. The method further comprises analyzing the measurement data to determine the volume of the fluid contained in the reservoir.

Performing the system check may comprise taking one or more baseline measurements using the fluid sensing unit. Performing the system check may further comprise confirming that the fluid sensing unit is in communication with a processing unit of the sensing reservoir. The sensing reservoir may further comprise one or more reservoir sensors, and performing the system check may comprise measuring one or more of a position, orientation, or motion of the sensing reservoir using the one or more reservoir sensors. The method may further comprise determining whether the sensing reservoir is in an inactive state based on the one or more of a position, orientation or motion of the sensing reservoir. The method may further comprise determining whether the sensing reservoir is undergoing excessive motion based on the one or more of a position, orientation or motion of the sensing reservoir.

The sensing reservoir may comprise one or more reservoir sensors, and generating the measurement data may further comprise measuring one or more of a position, orientation, or motion of the sensing reservoir with the one or more reservoir sensors, thereby determining an operating state of the sensing reservoir. The operating state of the sensing reservoir may comprise a filling state or a draining state. The one or more of a position, orientation, or motion of the sensing reservoir may comprise one or more of a vertical offset or a rotational offset of the sensing reservoir. The method may further comprise determining whether the sensing reservoir is in an acceptable orientation for generating the measurement data using the fluid sensing unit, based on the one or more of the vertical offset or the rotational offset of the sensing reservoir.

The fluid sensing unit may comprise one or more capacitive sensors, and generating measurement data may comprise measuring a capacitance of each of the one or more capacitive sensors. The measured capacitance may indicate of a level of fluid at each of the one or more capacitive sensors.

The fluid sensing unit may comprise a plurality of fluid sensors, and analyzing the measurement data may comprise determining a level of fluid at each of the plurality of fluid sensors, thereby determining a tilt of the sensing reservoir. Analyzing the measurement data may comprise calculating a volume of fluid contained in the sensing reservoir based on the measurement data generated by the fluid sensing unit, and measurement data generated by one or more reservoir sensors configured to measure one or more of a position, orientation, or motion of the sensing reservoir.

The sensing reservoir may further comprise one or more proximity sensors configured to detect one or more proximity triggers disposed within a predetermined distance from the one or more proximity sensors. The method may further comprise generating measurement data using the one or more proximity sensors to determine whether the sensing reservoir is coupled to a component comprising the one or more proximity triggers.

The method may further comprise setting the sensing reservoir in a standby state in response to a determination that the sensing reservoir is not coupled to the component, and setting the sensing reservoir in a measurement state in response to a determination that the sensing reservoir is coupled to the component. Steps of performing the system check, generating the measurement data using the fluid sensing unit, and analyzing the measurement data may be performed when the sensing reservoir is set in the measurement state.

The method may further comprise transmitting the measurement data generated using the fluid sensing unit or the volume of the fluid contained in the reservoir to another computing device in communication with the sensing reservoir.

These and other embodiments are described in further detail in the following description related to the appended drawing figures.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed systems, devices, and methods will now be described with reference to the drawings. Nothing in this detailed description is intended to imply that any particular component, feature, or step is essential to the invention. Although the present invention primarily relates to breast milk, any description herein of expression and collection of breast milk can also be applied to other types of fluids expressed from the breast, such as colostrum, or from other glands, organs, or anatomical regions of the body. Furthermore, the disclosed embodiments may be used in other applications, particularly applications involving the measurement of any fluids collected in a collection vessel.

Figure 1:
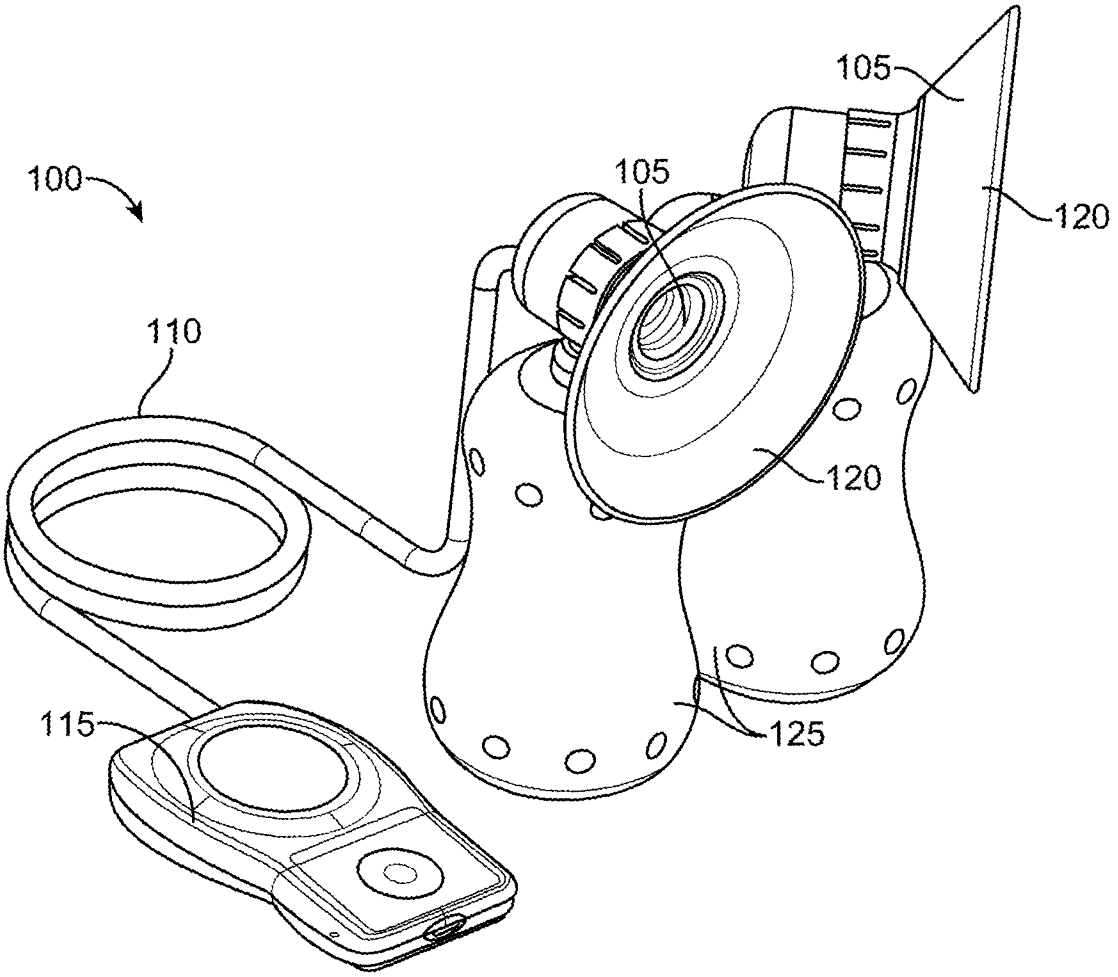
FIG. 1 is a perspective view of a pumping device suitable for use with present embodiments.

FIG. 1 illustrates an exemplary embodiment of a breast pump suitable for use with present embodiments. Pumping device 100 (also known as an "expression apparatus") includes breast interfaces 105, a tube 110, and a controller 115 (sometimes also referred to as a "pendant unit") operatively coupled to breast interfaces 105 through tube 110. Breast interfaces 105 include resilient and conformable flanges 120, for engaging and creating a fluid seal against the breasts, and collection vessels or reservoirs 125. Controller 115 houses the power source and drive mechanism for pumping device 100, and also contains hardware for various functions, such as controlling pumping device 100, milk production quantification, and communication with other devices, as described in further detail herein. Tube 110 transmits suitable energy inputs, such as mechanical energy inputs, from controller 115 over a long distance to breast interfaces 105. Breast interfaces 105 convert the energy inputs into vacuum pressure against the breasts in a highly efficient manner, resulting in the expression of milk into reservoirs 125. The device 100 may further comprise one or more sensors configured to track various characteristics of the collected fluid, as described in further detail herein. Power may be provided to the one or more sensors via a connection to the controller 115, or to another source of power.

In many instances, it can be desirable to measure and track various characteristics of the collected fluid such as expressed breast milk, such as the amount of milk production (e.g., volume, weight), expression frequency (e.g., time, date), and/or expression duration. In existing approaches, the tracking of milk production is commonly accomplished by manual measurements and record-keeping. Sensors integrated for use with a pumping device can provide digital-based means to automatically measure and track milk production for improved convenience, efficiency, and accuracy. For example, sensors can be used to measure the volume of expressed milk as volume per unit time, or total volume per pumping session.

Sensors for quantifying the composition of the expressed milk may also be provided with a pumping device. The composition of breast milk can be valuable information for understanding whether an infant is obtaining the appropriate amount of nutrition via the milk. This information can help mothers or clinicians identify whether additional nutrition should be supplied to the infant. Components of breast milk considered to be nutritionally important include carbohydrates such as glucose and lactose, fats such as triglycerides, proteins such as lactoferrin, organic acids such as taurine, vitamins such as vitamin D, and minerals such as zinc, copper, and iron. Sensors may be provided for measuring the relative amounts of one or more of such components in the expressed milk. Sensors may also be configured to determine the estimated caloric value of the expressed milk and/or the percentage of alcohol, drugs, or other contaminants present in the milk. Such sensors may include devices that can spectroscopically measure the presence of certain compounds in a volume of breast milk, or devices that can measure the enzymatic activity produced by certain compounds of breast milk that act as substrates for specific enzymes.

The one or more sensors may be coupled to a pumping device, such as to one or more portions of a breast interface. In embodiments in which the one or more sensors are coupled to one or more portions of the breast interface, the sensors may be further coupled to the pump controller via one or more communication lines configured to transmit signals between the sensors and the controller. Alternatively, the sensors may be coupled wirelessly to the controller or to a mobile device configured to control the pumping device, for example via a communication module coupled to the sensors. Embodiments of pumping devices having one or more sensors coupled thereto are disclosed in greater detail in U.S. patent application Ser. No. 14/616,557, the entire content of which is incorporated herein by reference.

The one or more sensors may also be provided in a separate accessory adaptable for use with various pumping devices, such as a sensing adaptor that can couple to a pumping device on one end, and to a reservoir on the other end. Such an adaptor may comprise sensors configured to measure one or more characteristics of the fluid as the fluid passes through the adaptor into a collection reservoir.

The one or more sensors may also be coupled to the fluid collection reservoir. For example, a reservoir may comprise an integrated fluid sensing unit configured to measure one or more characteristics of the fluid contained in the reservoir. Some embodiments of a sensing reservoir are disclosed in U.S. patent application Ser. No. 14/616,557, the entire content of which is incorporated herein by reference.

A sensing reservoir may be supplied with its own processing unit and power source, such that the sensing capability of the reservoir may function independently of the pumping device. Providing a sensing capability in an accessory, such as a reservoir, completely separate from the pumping device can have many benefits for users. The sensing reservoir may be adaptable for use with various pumping devices, including many commercially available systems, providing a great range of flexibility for users. For example, a user may choose to add the sensing reservoir to a pumping system she already owns, in order to gain the benefits provided by an automatic fluid sensing function. In addition, in case of failure of one or more of its components, a stand-alone sensing reservoir may be easier to repair or replace than a sensor integrated into a pumping system.

The sensing reservoirs described herein may comprise collection vessels configured to couple to a pumping device for collecting expressed breast milk. Alternatively or in combination, the reservoirs may comprise bottles configured to couple to an outlet mechanism, for example a baby bottle coupled to a feeding nipple for feeding an infant. The sensing reservoirs can include one or more sensors for generating measurement data indicative of one or more characteristics of milk expression as described herein (e.g., volume of expressed milk, composition of the expressed milk, etc.). The sensors may be configured to generate the measurement data at set intervals over time, and/or at the occurrence of specific events as detected automatically or as directed by a user. Any description herein pertaining to measurement of volume can also be applied to measurements of any other characteristics, and vice-versa. Any suitable type of sensor can be used, such as accelerometers, Hall effect sensors, photodiode/LED sensors, CCD sensors, cameras and other imaging devices, capacitive sensors, strain gauges, etc., and such sensors can be used in any number and combination. The sensors can be positioned at any location on the reservoir suitable for measuring the fluid contained in the reservoir.

A processing unit may be suitably combined with any sensing reservoir described herein, wherein the processing unit may be configured to receive data from the sensor and store the data, analyze the data, and/or transmit the data to another device. A sensing reservoir having an integrated sensor and processing unit can help automate the management and monitoring of milk production, thus reducing the need for manually maintaining records related to milk production. For example, a sensing reservoir can monitor the quantity of milk produced, and automatically process and send the data to a computing device, from which the user may easily access the information. A sensing reservoir as described herein may also be used to monitor the quantity of milk consumed by an infant. Such a system can greatly improve convenience for the users, and also help reduce human errors related to manual record maintenance. System and methods for managing an inventory of expressed breast milk, suitable for incorporation with the fluid measurement devices and methods disclosed in the present application, are disclosed in further detail in co-pending U.S. patent application Ser. No. 14/858,924, incorporated herein by reference in its entirety.

Figure 2A:
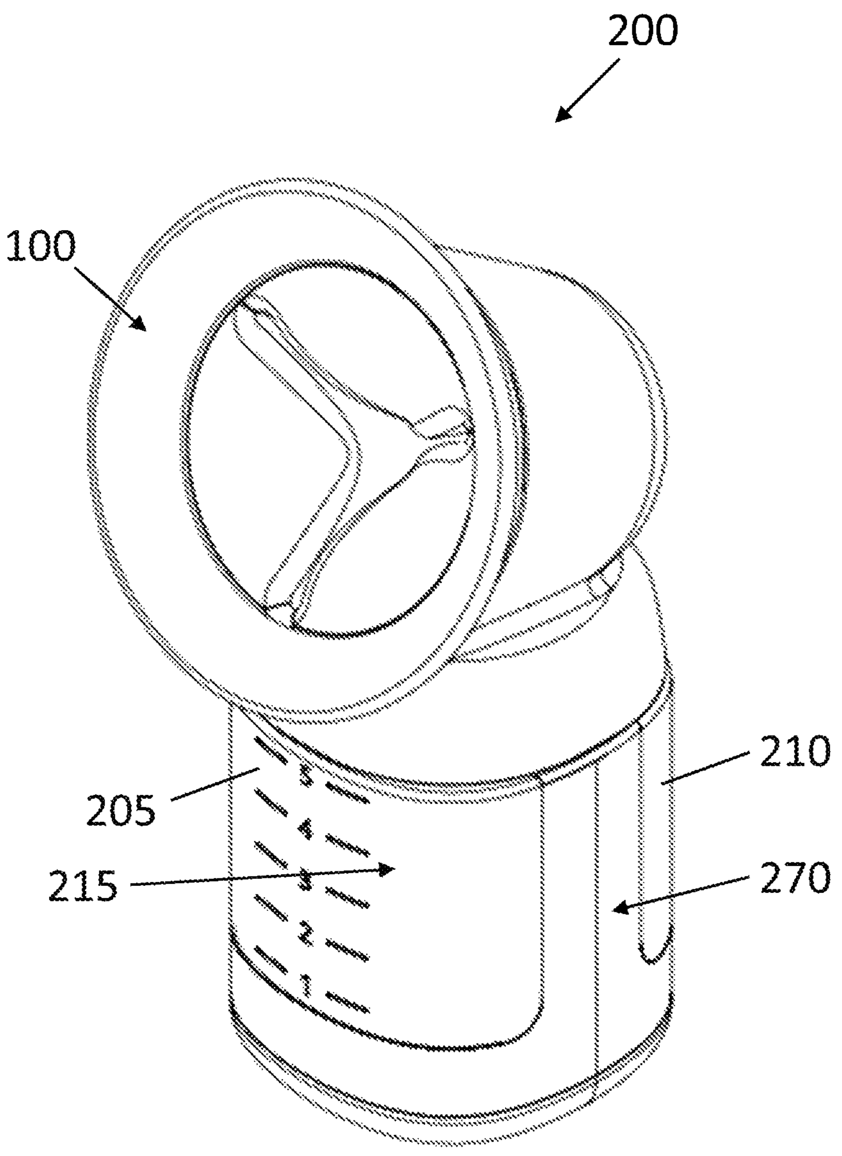
FIG. 2A is a perspective view of an exemplary embodiment of a sensing reservoir coupled to a pumping device.

FIG. 2A shows an exemplary embodiment of a sensing reservoir 200 coupled to a pumping device 100. The sensing reservoir 200 comprises a reservoir 205, the reservoir having a wall 210 that defines a chamber 215. The chamber is configured to contain a fluid, such as breast milk. The chamber can have a controlled or known geometry, such that the relationship between fluid level and the volume of fluid contained is known. Such a relationship may be known for the reservoir in a substantially upright position, as shown in FIG. 2A, as well as for the reservoir in a substantially inverted position. The sensing reservoir 200 further comprises a fluid sensing unit 270, configured to generate measurement data indicative of a characteristic of the fluid contained in the reservoir. In many embodiments, the fluid sensing unit comprises one or more sensors configured to generate measurement data indicative of a volume of the fluid contained in the reservoir. Alternatively or in combination, the fluid sensing unit may comprise one or more sensors configured to generate measurement data indicative of one or more properties of the fluid, such as a composition or nutritional content of breast milk. The fluid sensing unit may be coupled to the wall of the reservoir 205, or may be disposed at any other location suitable for measuring the contained fluid.

The fluid sensing unit may comprise one or more sensors of many types and configurations. In preferred embodiments, the fluid sensing unit comprises a capacitive sensor coupled to the wall of the reservoir, configured to measure a change in capacitance affected by the fluid in proximity to the capacitive sensor, as described in further detail herein. Alternatively or in combination, the fluid sensing unit may comprise one or more of other types of sensors. For example, the fluid sensing unit may comprise a strain gauge to measure a strain placed on the gauge by the fluid contained in the reservoir, wherein the strain gauge may be coupled to a bottom of the reservoir or to a valve disposed adjacent the opening of the reservoir. The fluid sensing unit may comprise an accelerometer disposed on a valve adjacent the reservoir opening, the accelerometer configured to measure the motion of the valve to determine the quantity of fluid passing through. The fluid sensing unit may comprise a beam-break sensor disposed adjacent the opening of the reservoir, configured to generate a signal when a fluid breaks a beam by passing between a beam emitter and a beam detector. The fluid sensing unit may comprise an image sensor coupled to the opening of the reservoir or to a portion of the wall, the image sensor configured to capture images of the fluid to quantify fluid volume.

The sensing reservoir 200 can measure the contained fluid while the sensing reservoir is in a filling state as shown in FIG. 2A, wherein the reservoir is in a generally upright position and fluid is being collected in the reservoir. For example, the sensing reservoir can operate in the filling state while the reservoir is coupled to a pumping device and collecting expressed breast milk, to measure the volume of breast milk expressed and collected in the reservoir. The sensing reservoir can further measure the fluid while the reservoir is in a draining state, wherein the reservoir is in a generally inverted position and fluid is being drained from the reservoir. For example, the sensing reservoir can operate in the draining state while the reservoir is coupled to a feeding attachment such as a feeding nipple and the contained breast milk is fed to an infant, thereby generating an indication of the volume of milk consumed by the infant. The sensing reservoir may be configured to determine the appropriate operating state, for example by sensing an orientation or tilt of the sensing reservoir, or by sensing the coupling of the reservoir to a pumping device or a feeding attachment, as described in further detail herein. Based on the determined operating state and the known geometry of the reservoir 205 and the chamber 215, appropriate algorithms may be applied in analyzing the measurement data generated by the fluid sensing unit, so as to compensate for the orientation of the reservoir and determine the correct volume of fluid contained in the reservoir.

Figure 2B:
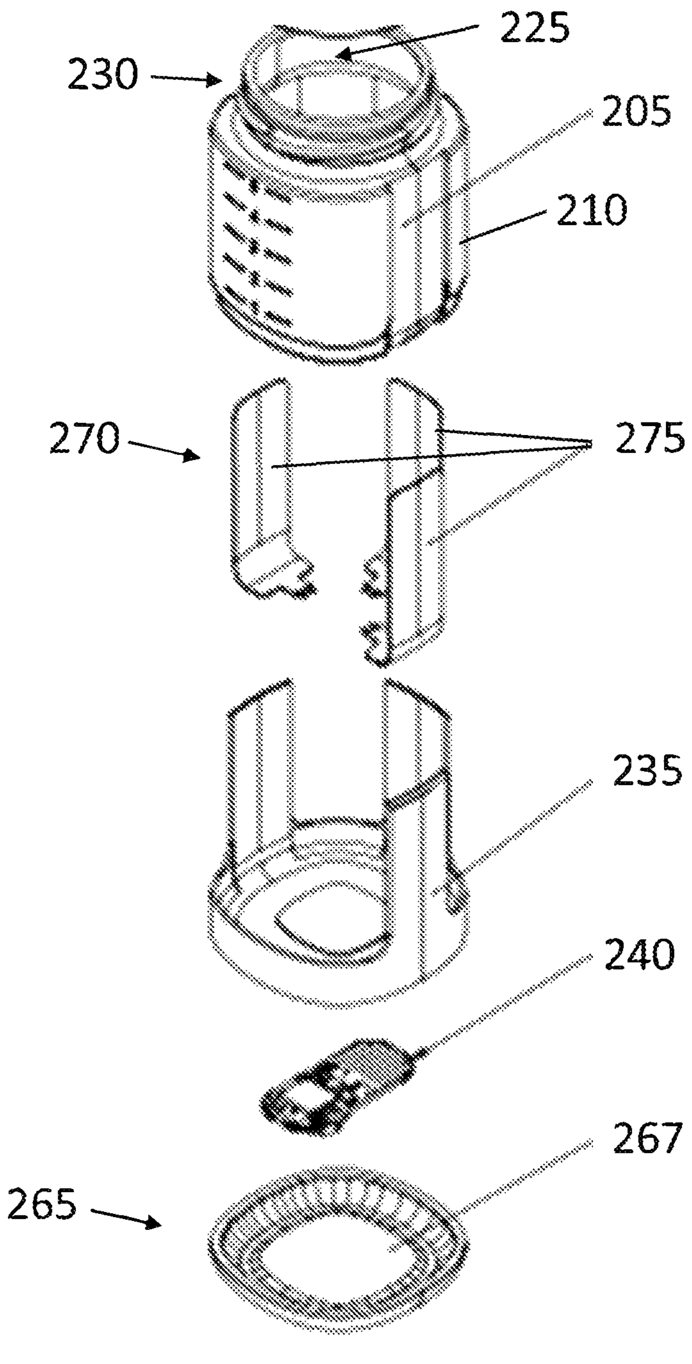
FIG. 2B shows an exploded view of a sensing reservoir, in accordance with embodiments.

FIG. 2B shows an exploded view of a sensing reservoir 200, in accordance with embodiments. The sensing reservoir comprises the reservoir 205 and the fluid sensing unit 270 coupled to a portion of the reservoir, such as the wall 210 of the reservoir. The sensing reservoir may further comprise an insulating unit 235, configured to encase the fluid sensing unit. The sensing reservoir may further comprise a processing unit 240, in communication with the fluid sensing unit 270 and configured to receive the measurement data generated by the fluid sensing unit. The processing unit and/or the fluid sensing unit may be powered by a power source (not shown) integrated with or coupled to the sensing reservoir. The sensing reservoir may further comprise a housing 265, configured to encase the electrical components of the sensing reservoir such as the processing unit and/or the power source. For example, the housing 265 may comprise a bottom cap 267 configured to couple to the bottom of the reservoir 205, as shown in FIG. 2B. Optionally, the housing 265 may be further configured to encase at least a portion of the fluid sensing unit 270 and/or the insulating unit 235. The housing may be fixedly coupled to the fluid sensing unit, insulating unit, the processing unit, and/or the power source, and removably couplable to the reservoir 205, such that the reservoir 205 may be an interchangeable component of the sensing reservoir 200.

The reservoir 205 comprises an opening 225 configured to allow passage of the fluid in and out of the reservoir. The opening 225 comprises a coupling mechanism 230, configured to removably couple to another device such as the pumping device 100 or feeding nipple. The coupling mechanism may comprise any coupling mechanism known in the art, such as screw threads, quarter turn couplings, bayonet couplings, interference fits, and the like. In preferred embodiments, the coupling mechanism comprises male screw threads, so as to make the sensing reservoir widely adaptable for use with many off-the-shelf pumping devices utilizing screw threads to attach a collection vessel to the pumping device. The reservoir 205 may further comprise one or more additional openings, such as vent openings to allow passage of air and thereby facilitate passage of the fluid through the opening 225.

The fluid sensing unit 270 may comprise one or more fluid sensors 275, distributed about the reservoir 205 in a known manner. For example, the fluid sensors 275 may be distributed about the periphery of the reservoir at a known rotational offset, as shown in FIG. 2B. For example, the fluid sensing unit may comprise three fluid sensors, the first fluid sensor offset at a 90° angle from the second sensor, and the third sensor offset at a 180° angle from the second sensor. In some embodiments, the fluid sensing unit comprises a plurality of fluid sensors distributed about the periphery of the reservoir at a substantially equal rotational offset from one another, such that the position of the fluid in the reservoir can be accurately determined. For example, the fluid sensing unit may comprise three fluid sensors rotationally offset at 120° angles from one another. In embodiments comprising three fluid sensors, the fluid position and reservoir orientation can be determined via triangulation of the fluid level sensed by each fluid sensor, as described in further detail herein. In some embodiments, the fluid sensing unit comprises a single fluid sensor.

The fluid sensing unit 270 may be coupled to the reservoir 205 in a manner that enables accurate measurement of the interior surface of the reservoir. For example, the one or more fluid sensors 275 may be placed on the interior surface of the reservoir for direct exposure to the fluid, or the fluid sensors placed on the interior reservoir surface may be covered with a thin film coating. In preferred embodiments, the fluid sensing unit is embedded in the wall of the reservoir, such that the fluid sensors are closer to the interior surface than to the external surface of the reservoir. While embodiments described herein are directed to a fluid sensing unit coupled to the wall of the reservoir, a fluid sensing unit may be coupled to any suitable location on the sensing reservoir.

The fluid sensing unit 270 may be fixedly coupled to the reservoir, in a manner that protects the component sensors from signal interference or damage. Alternatively, the fluid sensing unit may be removably couplable to the reservoir 205, such that the sensing unit may, for example, be removed from the reservoir while the reservoir is washed and/or sterilized. Optionally, the fluid sensing unit may be fixedly coupled to a housing that is removably couplable to the reservoir 205, wherein the housing is also coupled to electrical components of the sensing reservoir. For example, the fluid sensing unit and the processing unit and power source operably coupled thereto may be at least partially encased within a housing, which may be removably attached to a reservoir 205.

The sensing reservoir 200 may comprise a processing unit 240 in communication with the fluid sensing unit 270. The processing unit may be configured to receive measurement data from the fluid sensing unit and store the data, analyze the data, and/or transmit the data to another computing device, such as a smartphone, tablet, desktop computer, laptop computer, etc. The processing unit may perform analysis of the collected data and transmit the analyzed data to another device; alternatively, the processing unit may transmit raw measurement data to another computing device configured to perform the data analysis. The processing unit and/or the fluid sensing unit may be powered by a power source (not shown) such as a battery, operatively coupled to the processing unit. A housing 265 may be configured to surround the processing unit and/or the power source, in order to protect the electrical components. Optionally, the housing may also couple to or at least partially surround the fluid sensing unit 270. The housing may comprise a material with properties such that the housing can protect the encased structures from mechanical stresses and/or water damage. In some embodiments, the housing completely encases the housed components in a leak-proof manner to protect the components from water damage. The processing unit and/or power source may be fixedly coupled to the reservoir in a manner that can withstand mechanical stresses, extreme temperatures, and/or exposure to fluids (e.g., during milk expression or feeding or during washing of the sensing reservoir). For example, the electrical components can be encased in a housing having appropriate material properties, fixedly coupled to the reservoir via appropriate means (e.g., epoxy or cyanoacrylate adhesive bonding, ultrasonic welding, etc.). Alternatively, the processing unit and/or power source may be removably couplable to the sensing reservoir, such that the processing unit and/or power source may, for example, be removed from the reservoir while the reservoir is washed and/or sterilized. For example, the electrical components can be encased in a housing as described, wherein the housing may comprise a coupling mechanism that can be releasably coupled to the sensing reservoir.

Figure 2C:
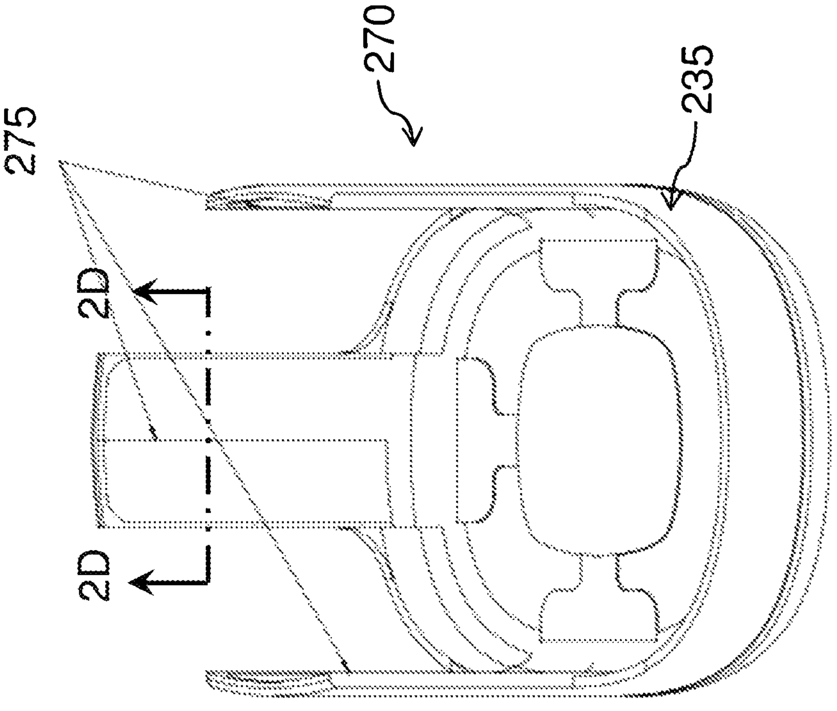
FIG. 2C shows an exemplary embodiment of a fluid sensing unit coupled to an insulating unit.

FIG. 2C shows an exemplary embodiment of a fluid sensing unit 270 coupled to an insulating unit 235. The insulating unit 235 can be configured to cover or encase the one or more fluid sensors 275 of the fluid sensing unit, thereby insulating the fluid sensing unit from external factors. For example, the insulating unit can provide electrical isolation of the sensors and protect the sensors from physical damage. The insulating unit can, for example, isolate the fluid sensors from the effects of physical contact with one or more human fingers holding the sensing reservoir during use. The insulating unit may comprise a material having a high electrical resistance, such as one or more plastics or rubbers or combinations thereof, or an air gap as described in further detail herein. The insulating unit can further provide protection against physical damage. For example, the insulating unit can comprise a material having properties to protect the encased sensors from mechanical stress, extreme temperatures, and/or water damage. The insulating unit may, for example, comprise one or more plastics or rubbers or combinations thereof, such as silicone. The insulating unit can be coupled to the reservoir so as to form a fluid tight seal around the fluid sensing unit, such that the sensing reservoir may be exposed to fluids (e.g., during milk expression or feeding or during washing of the sensing reservoir) without adversely affecting the function of the encased fluid sensors. Further, the insulating unit can provide improved aesthetics and/or user ergonomics, such as a comfortable grip feature.

Figure 2D:
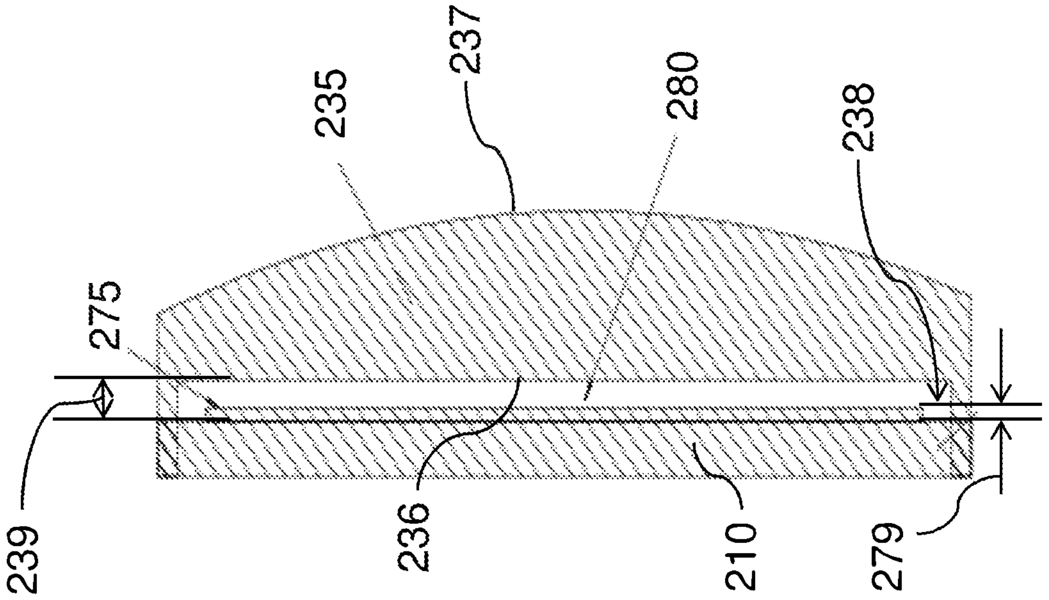
FIG. 2D is a cross-sectional view of the fluid sensing unit coupled to an insulating unit as shown in FIG. 2C.

FIG. 2D is a cross-sectional view of the fluid sensing unit 270 coupled to an insulating unit 235 as shown in FIG. 2C, along line 2D-2D. In preferred embodiments, the insulating unit 235 is coupled to the wall 210 of the reservoir in a manner that establishes an air gap 280 between the fluid sensor 275 and the insulating unit. For example, the insulating unit may comprise an internal surface 236 and an external surface 237 opposite the internal surface, the internal surface configured to face the reservoir wall 210 when coupled to the reservoir 205 and the external surface configured to face away from the reservoir wall when coupled to the reservoir. When the insulating unit is coupled to the reservoir, the reservoir wall 210 and the internal surface 236 of the insulating unit may collectively define a cavity 238 therebetween, the cavity configured to receive a fluid sensor 275 therein. The insulating unit may be shaped and sized to define the cavity 238 having a thickness 239 that is greater than a thickness 279 of a fluid sensor 275 disposed within the cavity. Thus, when the fluid sensor 275 is placed within the cavity and flush against the external surface of the reservoir wall 210, as shown in FIG. 2D, the air gap 280 may be established between the fluid sensor 275 and the internal surface 236 of the fluid sensing unit. The air gap can provide an area of constant dielectric strength, separating the fluid sensor from any interfering signals that may contact the insulating unit (e.g., human fingers, water or milk). The electrical isolation provided by the air gap can help improve the accuracy of the measurements made by the fluid sensors.

In many embodiments, the sensing reservoir 200 further comprises one or more reservoir sensors, configured to measure a position, orientation, and/or motion of the reservoir. For example, reservoir sensors may comprise one or more accelerometers configured to detect motion of the sensing reservoir. Alternatively or in combination, the reservoir sensors may comprise one or more gyroscopes configured to detect an orientation of the sensing reservoir. The one or more reservoir sensors can improve the accuracy of fluid measurement by the fluid sensing unit. As described in further detail herein, reservoir sensors that provide the orientation of the sensing reservoir can enable an algorithmic compensation for the reservoir orientation, thereby increasing the accuracy of fluid volume calculation based on the fluid levels detected by the fluid sensors. Often, the top portion of a reservoir chamber can have a different geometry than the bottom portion of the reservoir chamber, such that the translation between fluid level and contained fluid volume depends on whether the reservoir is substantially upright or inverted. Reservoir sensors configured to determine whether the reservoir is in an upright or inverted configuration can thus facilitate the selection of the correct translation algorithm in performing analysis of the fluid sensor data. Further, reservoir sensors can enable the sensing reservoir to switch from one operating state to another. For example, reservoir sensors configured to measure a position or motion of the sensing reservoir can determine when the reservoir is in an inactive/standby or "sleep" state, filling state, draining state, or in transition between one operating state to another. The fluid sensing unit can be configured to pause data collection during times the reservoir is determined to be in a standby or sleep state, so as to reduce power consumption and the collection of redundant data points. Further, the fluid sensing unit may be configured to collect data only during times the reservoir is determined to be in a stable filling state or draining state without excessive detected motion, so as to reduce the collection of unusable (e.g., excessively noisy) data points.

The reservoir sensors may be disposed on any portion of the sensing reservoir. For example, the reservoir sensors may be integrated with the fluid sensing unit 270. In preferred embodiments, the reservoir sensors are disposed on the processing unit 240, and in communication with a microcontroller or microprocessor of the processing unit.

Optionally, the sensing reservoir 200 may further comprise a means for detecting the coupling of the sensing reservoir to another component, such as a pumping device, a feeding attachment, or a storage cap. The detection of the coupling may be used as a cue for the fluid sensing unit and/or the reservoir sensors to initialize the system, determine the appropriate operating state, and begin sensor interrogation, enabling the sensing reservoir to switch quickly and accurately between different operating states (e.g., standby/sleep, filling, draining) and thereby optimize the efficiency of power consumption by the sensing reservoir. In some embodiments, the means for detecting the coupling may comprise one or more proximity sensors coupled to the sensing reservoir, and one or more corresponding proximity triggers coupled to a component to be coupled to the reservoir. The proximity sensors may be located near the portion of the reservoir configured to couple to the component, and the proximity triggers may be located near the portion of the portion of the component configured to couple to the sensing reservoir, such that the sensors and the triggers are brought into proximity when the sensing reservoir is coupled to the component. The proximity sensor may be configured to detect the proximity trigger when the proximity trigger is placed within a predetermined distance from the proximity sensor. When the component comprising the proximity trigger is coupled to the sensing reservoir, the proximity trigger is brought within the predetermined distance from the proximity sensor, thus enabling the proximity sensor to detect the coupling of the component to the sensing reservoir.

The proximity sensors and proximity triggers may be provided in various configurations in order to enable identification of the component that is coupled to the sensing reservoir. Thus, the sensing reservoir may be able to distinguish between the coupling of the reservoir to a feeding attachment or to a pumping device, enabling the system to determine the operating state of the sensing reservoir (e.g., whether the reservoir is about to begin filling (when attached to pumping device) or draining (when attached to feeding attachment)). In this case, the detection of a coupling event can not only direct the system to begin interrogation of the fluid sensing unit, but also help the processing unit select the appropriate analysis algorithm for the calculation of fluid levels based on the measurement data produced by the fluid sensing unit. The proximity sensor-derived operating state information can be cross-checked against the operating state information derived from the reservoir sensors and/or the fluid sensing unit to verify the current operating state (e.g., standby, filling, draining) of the sensing reservoir.

In some embodiments, a proximity sensor may comprise a combination of one or more light emitting diodes (LEDs) or other suitable light sources and one or more photodiodes. In such a system, a proximity trigger may comprise one or more highly reflective markers, disposed at predetermined locations with respect to the LED/photodiode sensor assembly when the component comprising the proximity trigger is coupled to the sensing reservoir. To detect the coupling of the sensing reservoir to the component, the LEDs may emit light directed towards the predetermined location of the component. When the sensing reservoir is not coupled or is coupled improperly or incompletely to the component, light emitted from the LEDs misses the reflective markers, hits only a relatively small portion of the reflective markers, and/or hits the reflective markers at a distance that is too far for reflected light to reach the photodiode. In this case, the photodiode detects no or little reflected light, below a pre-designated threshold intensity that indicates light reflection from the reflective markers. Accordingly, the measurement by the proximity sensor indicates that the sensing reservoir is not properly connected to the component. When the sensing reservoir is properly coupled to the component, light emitted from the LEDS hits at least a substantial portion of the reflective markers at an appropriate distance, such that at least a substantial portion of the emitted light is reflected back towards the LED/photodiode assembly. In this case, the photodiode detects reflected light at a high intensity, above the pre-designated threshold value, indicating the light has been reflected from the reflective markers. Accordingly, the measurement by the proximity sensor indicates that the sensing reservoir is properly connected to the component.

In some embodiments, a proximity sensor may comprise one or more Hall effect sensors configured to measure the intensity of a magnetic field. In such a system, a proximity trigger may comprise one or more magnets of predetermined magnetic strengths. The one or more magnets may be embedded in the component such that when the sensing reservoir is properly coupled to the component, the Hall effect sensors can sense the magnetic field generated by the one or more magnets. When the Hall effect sensors output voltage above a predetermined threshold corresponding to the predetermined magnetic strength of the magnet, the system may indicate that the sensing reservoir is properly connected to the component.

In some embodiments, a proximity sensor may comprise one or more reed switches configured to electrically on or off, or between a “connected” or “not connected” state, in response to detection of a magnetic field of a predetermined strength. In such a system, a proximity trigger may comprise one or more magnets of the predetermined magnet strengths. The one or more magnets may be embedded in the component such that when the sensing reservoir is properly coupled to the component, the reed switch can sense the magnetic field generated by the one or more magnets. When the reed switch “switches” in response to the detection of a magnetic field above the threshold strength, the system may indicate that the sensing reservoir is properly connected to the component.

The identity of the component that is coupled to the sensing reservoir may be determined in many ways. In some embodiments, different types of components may be associated with different predetermined threshold values of sensor output. For example, in embodiments comprising LED/photodiode assemblies as the proximity sensors and reflective markers as the proximity triggers, different predetermined threshold values of reflected light intensity may be set for different types of components. A pump device may comprise one or more first reflective markers having a first reflective index, while a feeding attachment may comprise one or more second reflective markers having a second reflective index different from the first reflective index. The processing unit may be pre-programmed with a first threshold value corresponding to the intensity of light reflected from the first reflective markers, and a second threshold value corresponding to the intensity of light reflected from the second reflective markers. Thus, when the intensity of light detected by the photodiode is substantially similar to the first threshold value, the processing unit may determine that the reservoir is connected to a pump device, and when the intensity of light detected by the photodiode is substantially similar to the second threshold value, the processing unit may determine that the reservoir is connected to a feeding attachment. Similarly, in embodiments comprising Hall effect sensors as the proximity sensors and magnets as the proximity triggers, different predetermined threshold values of magnetic field strength may be set for different types of components. To produce different sensor outputs between different types of components, proximity triggers with varying signal levels may be used (e.g., reflective markers with different reflective indexes, magnets with different magnetic strengths), and/or different numbers or areas/sizes of proximity triggers may be used.

In some embodiments, different types of components may be associated with proximity triggers disposed at different, known locations. The sensing reservoir may comprise a plurality of proximity sensors disposed at various locations of the reservoir corresponding to the different locations of proximity triggers on different components. For example, the sensing reservoir may comprise a first proximity sensor disposed at a first location of the reservoir, and a second proximity sensor disposed at a second location different from the first location. A pumping device may comprise a proximity trigger disposed at a location corresponding to the first location of the reservoir, and a feeding attachment may comprise a proximity trigger disposed at a location corresponding to the second location of the reservoir. Thus, when the pumping device is coupled to the sensing reservoir, the first proximity sensor detects a connection, whereas when the feeding attachment is coupled to the sensing reservoir, the second proximity sensor detects a connection. The processing unit may be pre-programmed with the associations between sensor locations and component types, such that the sensing reservoir can identify the type of component coupled to the reservoir based on the location of the proximity sensor that detects a connection.

Figure 3A:
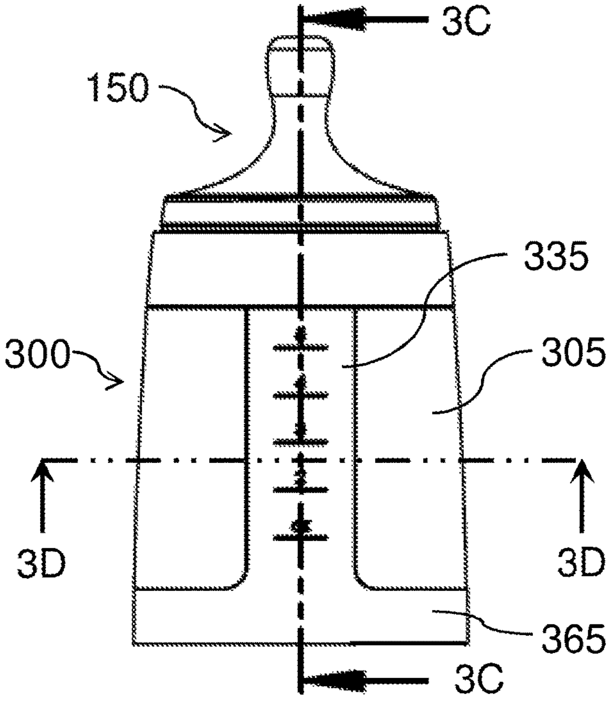
FIG. 3A is a side view of a sensing reservoir coupled to a feeding attachment.
Figure 3B:
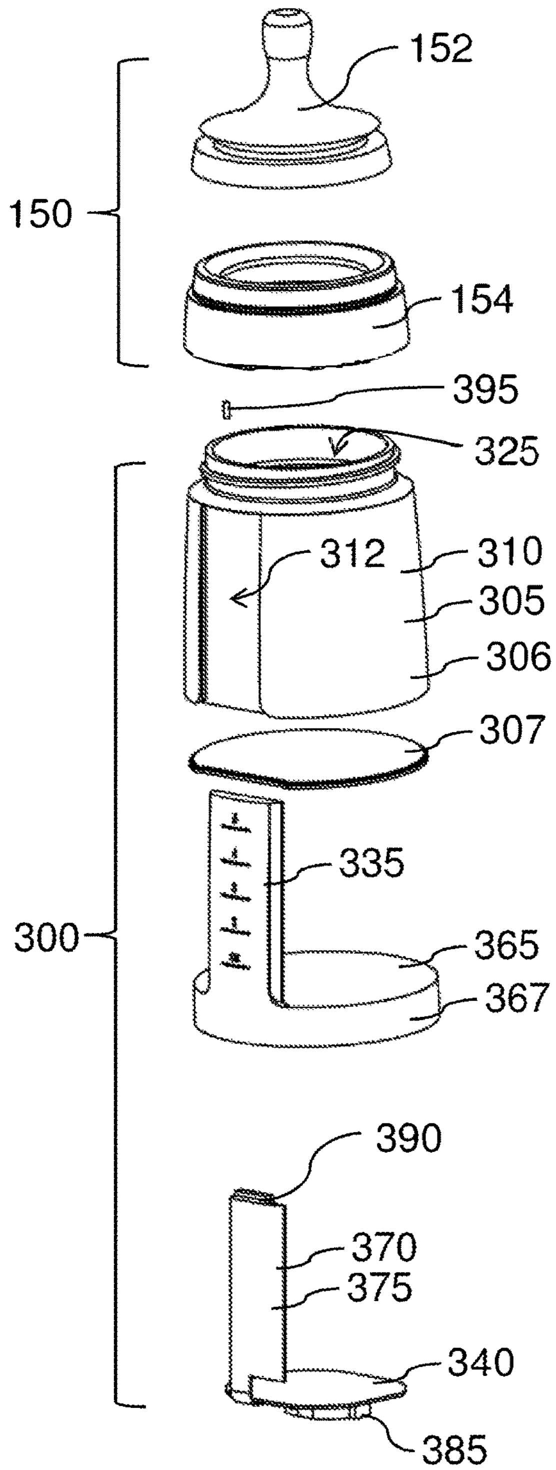
FIG. 3B is an exploded view of the sensing reservoir of FIG. 3A.
Figure 3C:
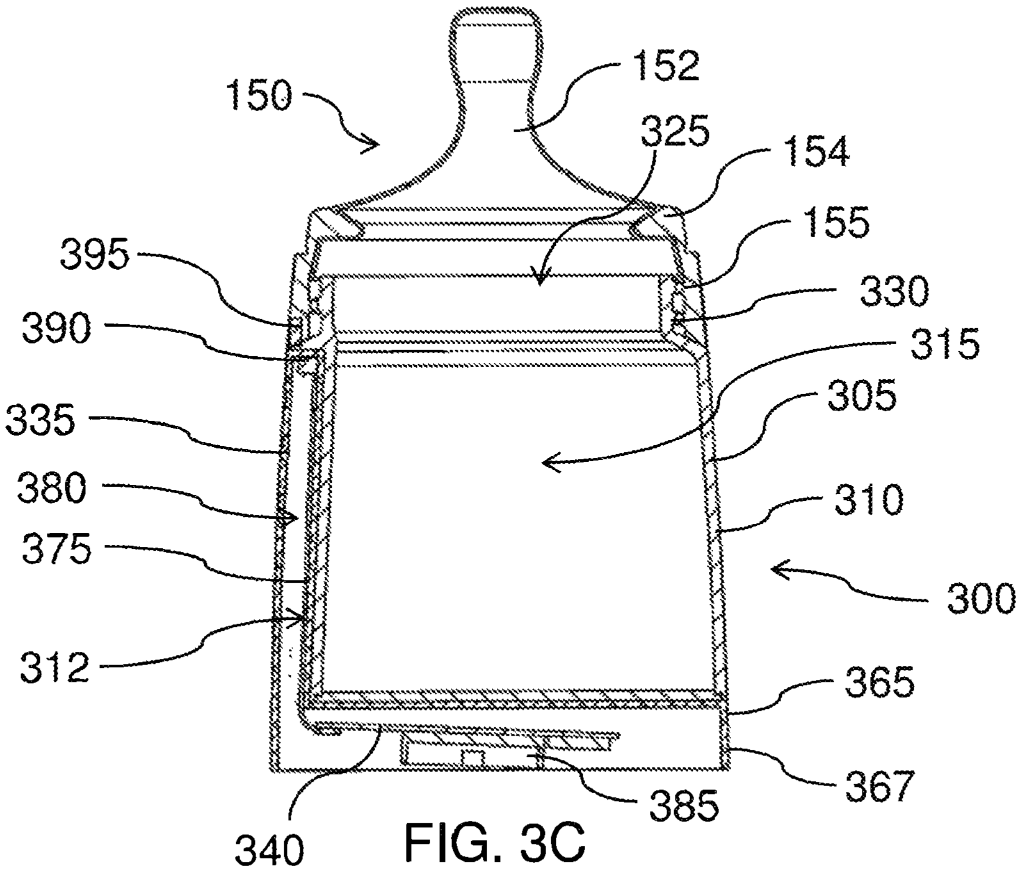
FIG. 3C is a vertical cross-section of the sensing reservoir of FIG. 3A along line 3C-3C.
Figure 3D:
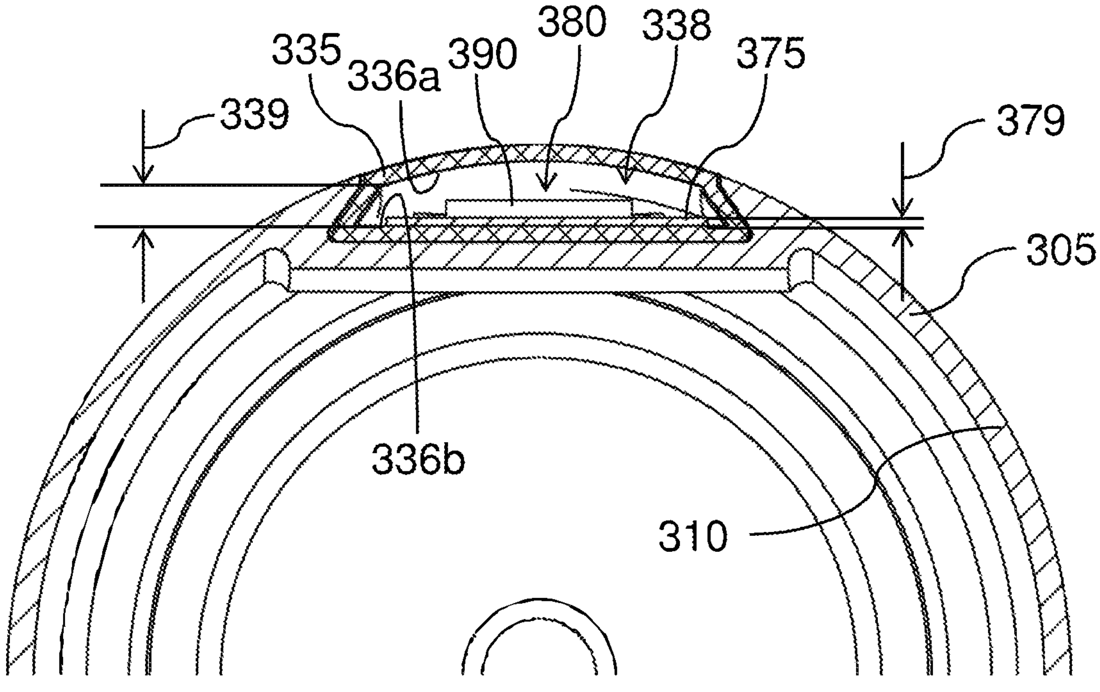
FIG. 3D is a horizontal cross-section of the sensing reservoir of FIG. 3A along line 3D-3D.

FIGS. 3A-3D illustrate an exemplary embodiment of a sensing reservoir 300 comprising a proximity sensor 390 and coupled to a feeding attachment 150. FIG. 3A is a side view of the sensing reservoir 300 coupled to the feeding attachment 150. FIG. 3B is an exploded view of the sensing reservoir 300 of FIG. 3A. FIG. 3C is a vertical cross-section of the sensing reservoir 300 of FIG. 3A along line 3C-3C. FIG. 3D is a horizontal cross-section of the sensing reservoir 300 of FIG. 3A along line 3D-3D. The sensing reservoir 300 can be similar in many aspects to the sensing reservoir 200 described with reference to FIGS. 2A-2D. For example, the sensing reservoir 300 may comprise a reservoir 305, a fluid sensing unit 370, an insulating unit 335, a housing 365, a processing unit 340, and one or more reservoir sensors (not shown), each of which may be similar in many aspects to the correspondingly-named component described with reference to sensing reservoir 200 of FIGS. 2A-2D. The sensing reservoir further comprises a power source 385 coupled to the processing unit 340. The sensing reservoir 300 further comprises one or more proximity sensors 390, and the feeding attachment 150 comprises one or more proximity triggers 395 configured to be detected by the one or more proximity sensors 390 when the feeding attachment is coupled to the sensing reservoir.

The feeding attachment 150 may comprise a feeding nipple 152 and a coupling adaptor 154 coupled together fixedly or removably. The feeding attachment may further comprise one or more proximity triggers 395, which may be embedded within the coupling adaptor as best shown in FIG. 3C. The coupling adaptor 154 may comprise a coupling mechanism 155, such as a threaded interior surface, configured to couple the adaptor to the reservoir 305.

The reservoir 305 may be coupled to the feeding attachment 150 via a coupling mechanism 330 disposed adjacent the opening 325 of the reservoir, the coupling mechanism 330 configured to couple to the coupling mechanism 155 of the coupling adapter 154. For example, the coupling mechanism 330 may comprises a threaded external surface configured to mate with a threaded interior surface of the coupling adaptor 154. The reservoir 305 may comprise two or more portions that can be fixedly coupled together to collectively define the chamber 315 of the reservoir. For example, the reservoir may comprise a body portion 306 and a bottom portion 307, wherein the bottom portion is configured to couple to the body portion, for example via a snap fit or a press fit. The reservoir wall 310 may define one or more recessed regions 312 on the external surface of the wall. The recessed region may be shaped to receive a fluid sensor therein, so that the fluid sensor can be embedded within the reservoir wall in close proximity to the interior surface of the reservoir wall. The recessed region may be shaped to receive the fluid sensor such that the sensor lays flush against the external surface of the reservoir wall. Optionally, the fluid sensor may be encased within an insulating unit as described herein, and the recessed region may be shaped to receive a portion of the insulating unit and the fluid sensor disposed therein such that an external surface of the insulating unit lays flush against the external surface of the reservoir wall. In embodiments of the fluid sensing unit comprising a plurality of fluid sensors, the reservoir may comprise a plurality of recessed regions, each of which may be shaped to receive each of the plurality of fluid sensors.

The fluid sensing unit 370 may comprise one or more fluid sensors 375 configured to measure information relating to the level of fluid contained inside the reservoir 305. For example, the fluid sensing unit may comprise one or more capacitive sensors as described in further detail herein. FIGS. 3A-3D show the fluid sensing unit 370 comprising a single fluid sensor 375 configured to be embedded in a wall of the reservoir 305. The fluid sensor 375 may be disposed within an insulating unit 335 configured to provide electrical isolation of the fluid sensor and protect the sensor from physical damage, as described herein. For example, as best shown in FIG. 3D, the insulating unit may be configured to establish an air gap 380 between the fluid sensor and the insulting unit when the fluid sensor is encased within the insulting unit. The insulating unit may comprise an internal surface 336 defining an internal cavity 338 configured to receive the fluid sensor 375 therein. The internal cavity 338 may have a minimum thickness 339 greater than the thickness 379 of the fluid sensor 375, such that when the fluid sensor is disposed within the cavity flush against a first internal surface 336*a* of the insulating unit, an air gap 380 is established between the fluid sensor and a second internal surface 336*b* opposite the first internal surface. In embodiments further comprising a proximity sensor 390 disposed within the insulating unit, as described in further detail herein, the thickness of the cavity 338 may also be greater than a thickness of the proximity sensor, such that an air gap is also established between the proximity sensor and an internal surface of the insulating unit. The insulating unit may be configured to couple to the reservoir 305 fixedly or removably, for example by fitting within one or more recessed regions 312 of the reservoir.

The sensing reservoir may further comprise one or more proximity sensors 390 configured to detect one or more corresponding proximity triggers. The one or more proximity sensors 390 may be disposed within the insulating unit 335 and/or coupled to the fluid sensing unit 370. For example, the proximity sensors may be coupled to a top end of the fluid sensor 375 and enclosed within the insulating unit 335, as shown in FIGS. 3B and 3C. In embodiments comprising capacitive fluid sensors having a conductive material printed onto a flexible circuit board, the proximity sensors may also be printed onto the same circuit board above the capacitive sensor.

As shown in the FIG. 3C, when the feeding attachment 150 is coupled to the sensing reservoir 300, the proximity sensor 390 is brought adjacent to the proximity trigger 395, such that the proximity sensor can detect the trigger and thereby determine that a connection to a component has been made. Further, as described herein, the proximity sensor can determine the type of component (e.g., feeding attachment) that has been coupled to the reservoir, thereby helping to identify the operating state of the reservoir (e.g., draining). The proximity sensor 390 and proximity trigger 395 may comprise any combination of proximity sensors and triggers as described herein, such as an LED/photodiode assembly and one or more reflective markers, a Hall effect sensor and one or more magnets, a reed switch and one or more magnets, or any other suitable combination of a sensor and an element capable to triggering a sensor output when the element is brought into proximity of the sensor.

The processing unit 340 may be operably coupled to the fluid sensing unit 370, proximity sensors 390, and/or reservoir sensors (not shown), and to a power source 385. As described herein, the processing unit may be configured to receive measurement data from the fluid sensing unit, reservoir sensors, and/or proximity sensors, store the data, analyze the data, and/or transmit the data to another computing device. The power source may be configured to provide power to the processing unit, fluid sensing unit, and the one or more proximity sensors. A housing 365 may be provided to surround and protect the processing unit and/or the power source, as described herein. The processing unit and power source may be enclosed within a bottom portion 367 of the housing, which may be sized and shaped to align with the bottom of the reservoir 305. Optionally, the insulating unit 335 and the housing 365 may comprise a single integrated component, configured to house the proximity sensors, fluid sensing unit, processing unit, and the power source. The single, integrated housing, containing all of the components of the sensing reservoir except the reservoir 305, may be removably couplable from the reservoir 305, so as to enable quick and easy exchange of the reservoir 305 (e.g., for washing/sterilization or replacement of the reservoir).

Figure 4A:
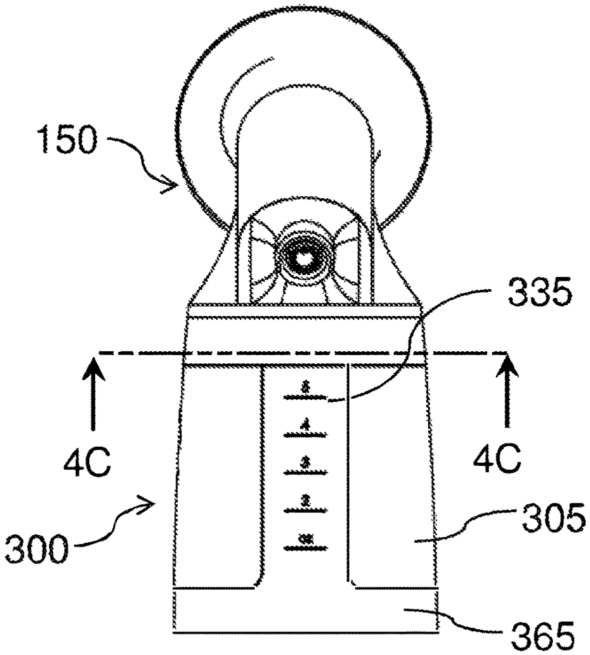
FIG. 4A is a side view of the sensing reservoir of FIGS. 3A-3D coupled to a pumping device.
Figure 4C:
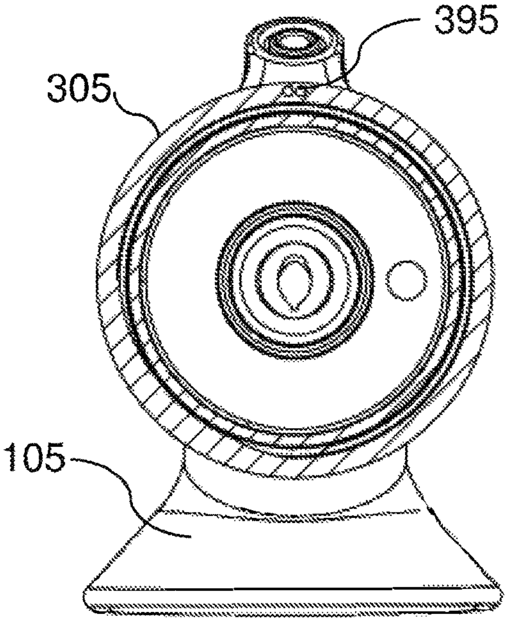
FIG. 4C is a horizontal cross-section of the sensing reservoir of FIG. 4A along line 4C-4C.
Figure 4B:
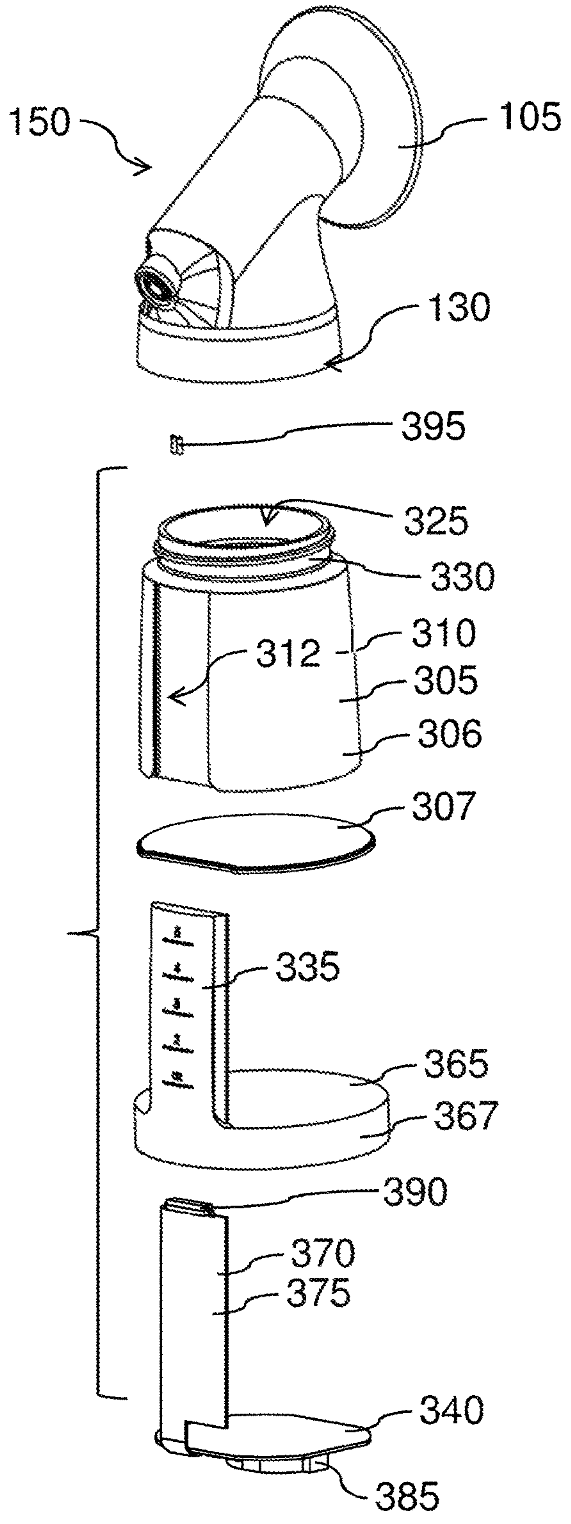
FIG. 4B is an exploded view of the sensing reservoir of FIG. 4A.

FIGS. 4A-4C illustrate the sensing reservoir 300 of FIGS. 3A-3D coupled to a pumping device 100. FIG. 4A is a side view of the sensing reservoir 300 coupled to the pumping device 100. FIG. 4B is an exploded view of the sensing reservoir 300 of FIG. 4A. FIG. 4C is a horizontal cross-section of the sensing reservoir 300 of FIG. 4A along line 4C-4C. The sensing reservoir 300 is substantially similar to the sensing reservoir 300 described with reference to FIGS. 3A-3D, but is coupled to a pumping device 100 instead of a feeding attachment.

The pumping device 100 may comprise a breast interface 105 configured to seal against a breast to express breast milk therefrom, and configured to couple to a collection vessel, such as the sensing reservoir 300, where expressed breast milk may be collected. The breast interface 105 may comprise a coupling mechanism 130 configured to mate with a coupling mechanism 330 of the reservoir 305, to couple the breast interface to the sensing reservoir. For example, the coupling mechanism 130 may comprise a threaded internal surface, and the coupling mechanism 330 of the reservoir 305 may comprise a threated external surface.

The pumping device 100 further comprises one or more proximity triggers 395 embedded within the breast interface 105 near the portion of the breast interface configured to couple to the sensing reservoir 300. In the embodiment shown in FIG. 4B, the breast interface comprises two proximity triggers 395, compared to the single proximity trigger 395 embedded in the feeding attachment 150 as shown in FIG. 3B. The different number of proximity triggers in the pumping device compared to the feeding attachment can help the proximity sensor 390 of the sensing reservoir 300 distinguish between the different components, as described in further detail herein. For example, in embodiments comprising a Hall effect sensor as the proximity sensor and one or more magnets as the proximity trigger, the feeding attachment may comprise one magnet while the pumping device may comprise two magnets, such that the proximity sensor produces output of different intensities when the different components are coupled to the sensing reservoir. Alternatively to using different numbers of proximity triggers, different locations of proximity triggers may also be used to distinguish between different components, as described herein.

Figure 5:
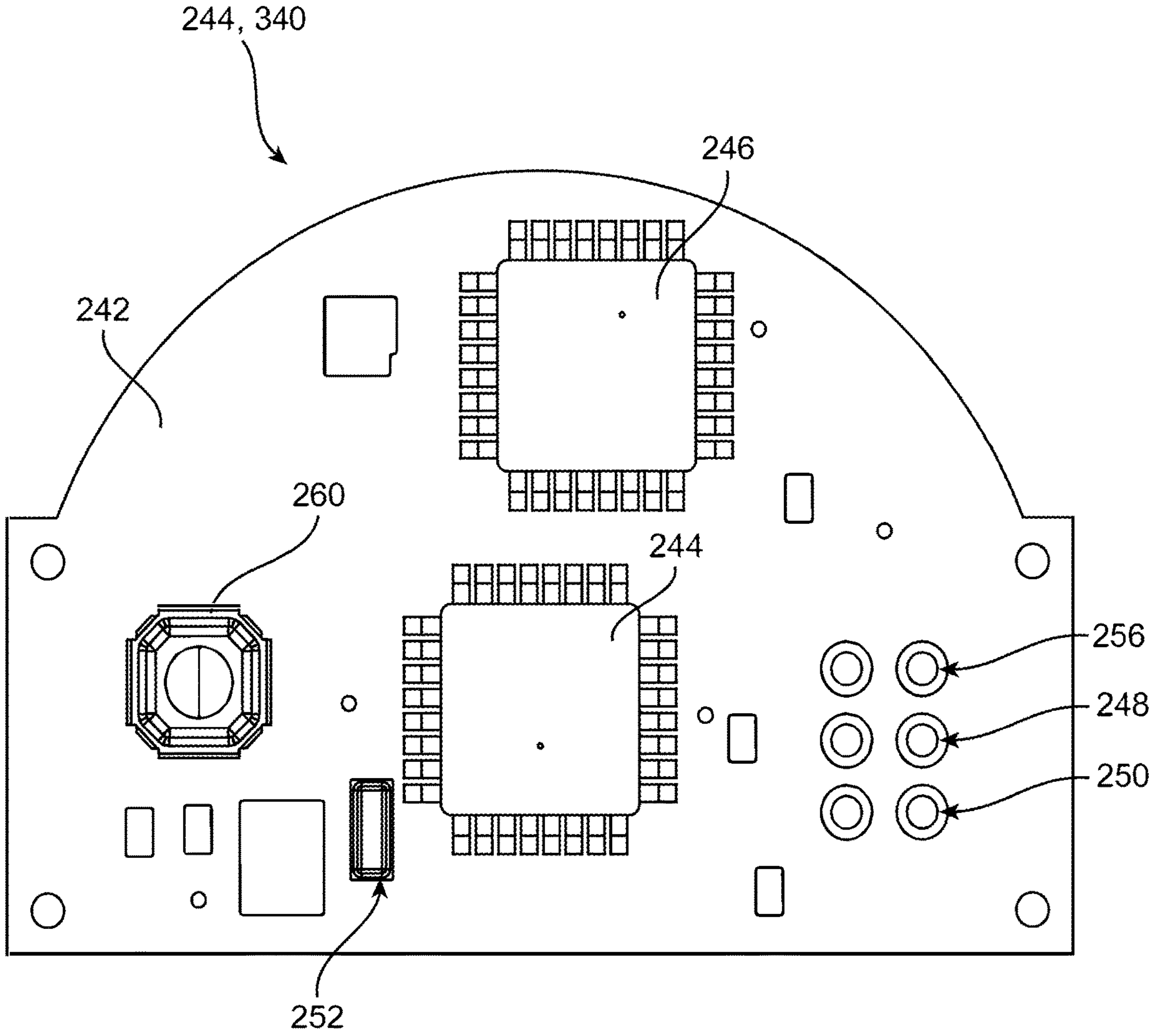
FIG. 5 is a top view of an exemplary embodiment of a processing unit suitable for incorporation with a sensing reservoir in accordance with embodiments.

FIG. 5 illustrates an exemplary embodiment of a processing unit suitable for incorporation with a sensing reservoir in accordance with embodiments. For example, the processing unit may comprise the processing unit 240 shown and described with reference to FIGS. 2A-2D, or the processing unit 340 shown and described with reference to FIGS. 3A-3D or 4A-4C. The processing unit may comprise one or more of a printed circuit board (PCB) 242 housing one or more of a microcontroller or microprocessor 244, a communication module 246, a fluid sensor connection 248, a power connection 250, a proximity sensor connection 256, and a timer 252. The processing unit may further comprise a memory (not shown). Power may be supplied to the processing unit via a power source comprising a battery or a direct contact connection such as a cable or pad connectors. Alternatively or in combination, power may be supplied via an inductive charging system comprising a battery and a wireless charger, which may be charged using an inductive charging method as known in the art.

The processing unit may receive signals from the fluid sensing unit through the fluid sensor connection 248, and the signals may be transmitted to the microprocessor 244. One or more reservoir sensors 260, configured to measure a position, orientation, and/or motion of the sensing reservoir, may also be disposed on the processing unit, and may transmit measured signals directly to the microprocessor 244. Optionally, the processing unit may also receive signals from one or more proximity sensors through the proximity sensor connection 256, and the signals may be transmitted to the microprocessor 244. The microprocessor may comprise a non-transitory computer readable medium comprising instructions to collect and process the signals received from the fluid sensing unit, the reservoir sensors, and/or the proximity sensors. The microprocessor may further comprise instructions to transmit the collected and/or processed signals to a memory for storage, or to the communication module 246 for transmission to another computing device. The communication module may comprise a wireless transmitter/receiver such as a Blue Tooth or a WiFi module, for example. The communication module may be configured to transmit the measurement data to another computing device, such as a mobile phone, tablet, or personal computer, for data analysis and/or display of the analyzed data to a user. Alternatively or in combination, the communication module may be configured to transmit the measurement data to a server for data analysis, and the server may transmit the analyzed data to a personal computing device for display to the user. The user may view and track the analyzed measurement data from the computing device, for example via a mobile application on a mobile phone.

Referring again to FIGS. 2A-2D, 3A-3D, and 4A-4C, in preferred embodiments, the one or more fluid sensors 275 or 375 of the fluid sensing unit 270 or 370 comprise one or more capacitive sensors. A capacitive sensor can measure the level of fluid in the reservoir, by detecting a change in capacitance affected by the dielectric permittivity of the fluid in proximity to the sensor. The capacitive sensor may be configured to measure self-capacitance, or parasitic capacitance, between the sensor and its surrounding environment. Alternatively or in combination, the capacitive sensor may be configured to measure mutual capacitance between one capacitive sensor and another capacitive sensor disposed nearby.

A liquid brought in close proximity to a capacitive sensor can change the self-capacitance of the sensor, based on the electrical properties of the liquid. Table 1 summarizes the dielectric constants of some common materials. Liquids such as water or milk generally have a dielectric permittivity greater than the dielectric permittivity of plastics commonly used in making collection reservoirs. Accordingly, the self-capacitance of a capacitive sensor embedded in the wall or otherwise coupled to the interior surface of a plastic reservoir can increase when a fluid such as breast milk is brought in proximity to the capacitive sensor.

TABLE 1

Dielectric constants of common materials.

| Material | Dielectric constant (ε) |
|---|---|
| Air | 1 |
| Glass | 5-10 |
| Polyethylene | 2.25 |
| Polypropylene | 2.2 |
| Silicone | 3.6 |
| Polycarbonate, molded | 2.8-3.4 |
| Polystyrene | 2.5-2.6 |
| Water, room temp. | 80.4 |

The change in the capacitance of a capacitive sensor may be observed by a microprocessor in communication with the sensor. A program or functional unit of the microprocessor can apply a signal to a pin that is coupled to the capacitive sensor. An analog circuit, such as an analog-to-digital converter (ADC), can sample and measure the voltage on the pin. The capacitance and resistance of the pin, the connection to the capacitive sensor, and the capacitive sensor itself can affect the speed with which the pin reaches the signal level. The microprocessor can record the time or count value required for the pin to reach the signal level. As the environment of the electrode changes, the amount of time required for the pin to reach the voltage level generally changes. For example, as fluid collects inside a reservoir, the self-capacitance of the capacitive sensor can increase, consequently increasing the time delay required for the pin to reach the voltage level. This increase in time delay, recorded by the microprocessor, can thereby indicate the increase in fluid level inside the reservoir.

FIGS. 6A-6H illustrates some exemplary configurations of a capacitive sensor 400 suitable for incorporation with a sensing reservoir. The capacitive sensor may comprise a conductive material, such as copper, aluminum, silver, indium tin oxide (ITO), or a combination thereof. The material may comprise solid sheet of material or a mesh, such as an optically clear silver mesh. The material may comprise a flexible polyimide.

FIGS. 6A-6D illustrate capacitive sensors having one or more continuous sensing regions configured to extend continuously along a length, such as the height, of the reservoir. Capacitive sensors with continuous sensing regions may be configured to measure self-capacitance, mutual capacitance between two adjacent sensing regions, or a combination of self-capacitance and mutual capacitance. For self-capacitance measurements, each continuous sensing region may be connected to the processing unit for read-out. For mutual capacitance measurements, one sensing region may be connected to the processing unit, while the adjacent sensing region may be charged to a known voltage. As the reservoir is filled with fluid and the level of fluid along the sensing region rises, the total capacitance of a sensor can change, and the change may be detected and recorded as described herein. In embodiments comprising two or more sensing regions, the spacing between two adjacent sensing regions may be configured to provide maximal mutual capacitance between the two sensing regions. The spacing may be constant or varying through the length of the sensing regions.

Figure 6A:
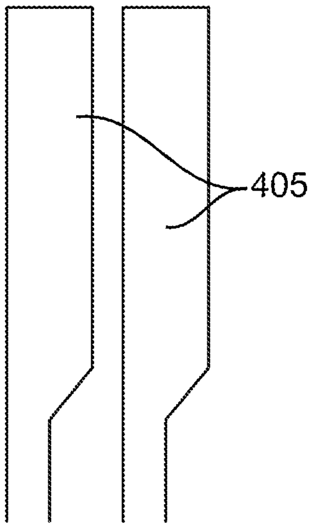
FIGS. 6A-6D illustrate capacitive sensors having one or more continuous sensing regions configured to extend continuously along a length of the reservoir.

FIG. 6A illustrates a capacitive sensor having continuous sensing regions 405 with a shape that is uniform through the length of a sensing region. A sensing region 405 may have a width configured to provide an area of the sensor sufficient for detecting changes in capacitance affected by the fluid contained in the reservoir. In embodiments of the capacitive sensor comprising two or more sensing regions 405, the two or more sensing regions may have the same width, or each sensing region may have a different width.

Figure 6B:
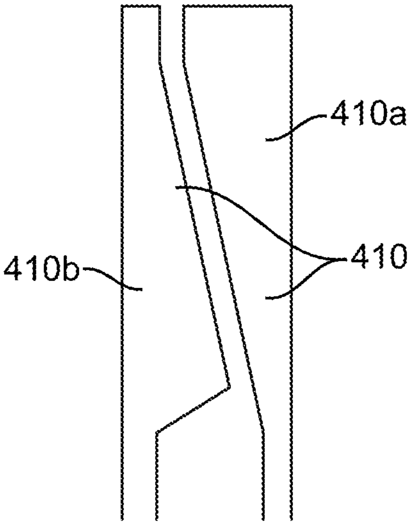

FIG. 6B illustrates a capacitive sensor having continuous sensing regions 410 with a shape that varies directionally along the length of a sensing region. For example, as shown in FIG. 6B, each of the sensing regions 410*a* and 410*b* may be shaped to increase in width from one end to the other end, such that the capacitive area of each sensing region increases from one end to the other end. The directionally varying shape of sensing regions 410 may help compensate for the saturation effect of the capacitive sensors, wherein the changes in capacitance can become more difficult to detect as the fluid level inside the reservoir reaches the maximal level, due to saturation of capacitance of the sensors. The capacitive sensor may comprise two or more directionally varying sensing regions 410*a* and 410*b* having complementary shapes, such that the sensor may provide compensation for the saturation effect whether the reservoir is in an upright or inverted orientation. In the embodiment shown in FIG. 6B, sensing region 410*a* can provide a larger capacitive area at high fluid levels while the reservoir is in a substantially upright orientation. Similarly, sensing region 410*b* can provide a larger capacitive area at high fluid levels while the reservoir is in a substantially inverted orientation.

Figure 6C:
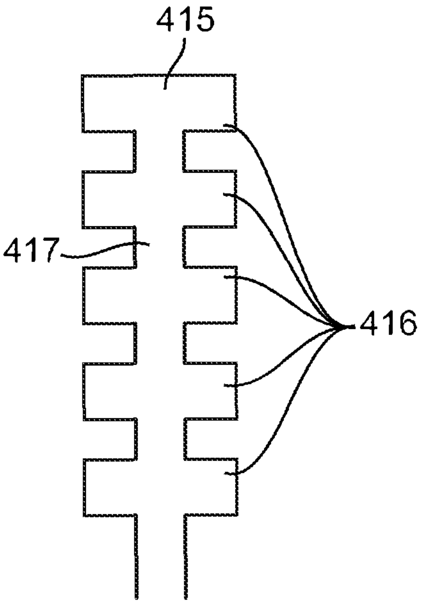
Figure 6D:
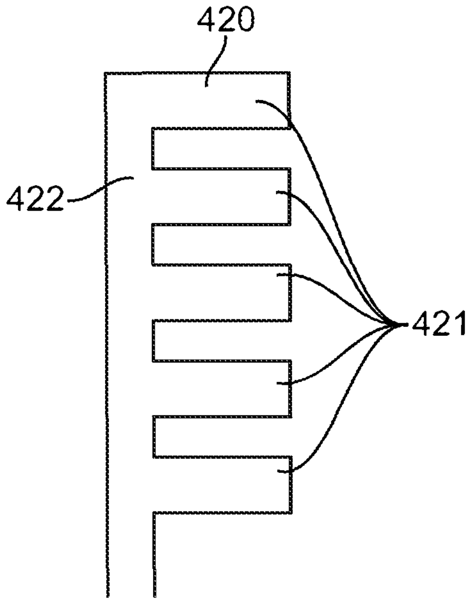

FIGS. 6C and 6D illustrate capacitive sensors comprising multi-fingered sensing regions. FIG. 6C shows a multi-fingered sensing region 415 comprising a plurality of fingers 416 connected to a stem 417, the stem configured to extend through the middle of the fingers 416. FIG. 6D shows a multi-fingered sensing region 420 comprising a plurality of fingers 421 connected to a stem 422, the stem configured to extend through one side of the fingers 421. Each finger may be configured to have a greater width than the stem, such that each finger provides a larger capacitive area than the portion of the stem preceding the finger. As fluid fills the reservoir and the fluid level passes between the fingers of a single sensing region through a stem portion, small capacitance changes may be observed. As the fluid covers the region of a finger, a larger and more perceptible change may be observed. This discrete change can facilitate the detection of fluid level changes. While FIGS. 6C and 6D depict fingers of a sensing region having a uniform size and shape, the size and/or shape of the fingers may vary within a single sensing region. For example, the fingers may be configured to increase in area from one end of the sensing region to the other, in order to compensate for the saturation effects of the capacitive sensor as described in relation to the embodiments of FIGS. 6A and 6B. In addition, single capacitive sensor may comprise two or more multi-fingered sensing regions having complementary patterns, configured to interlock with constant or varying spacing between the sensing regions. The multi-fingered shape of the sensing regions can help increase the mutual capacitance between the two sensing regions, by providing a greater total capacitive area between the sensing regions.

Figure 6E:
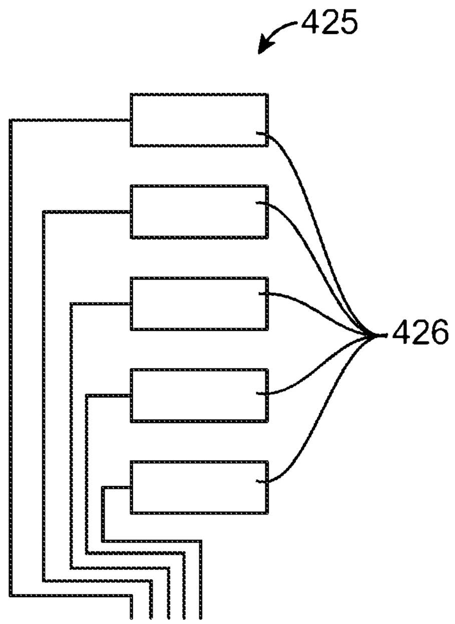
FIGS. 6E and 6F illustrate capacitive sensors having a plurality of discrete sensing regions configured to be placed along the length of the reservoir.
Figure 6F:
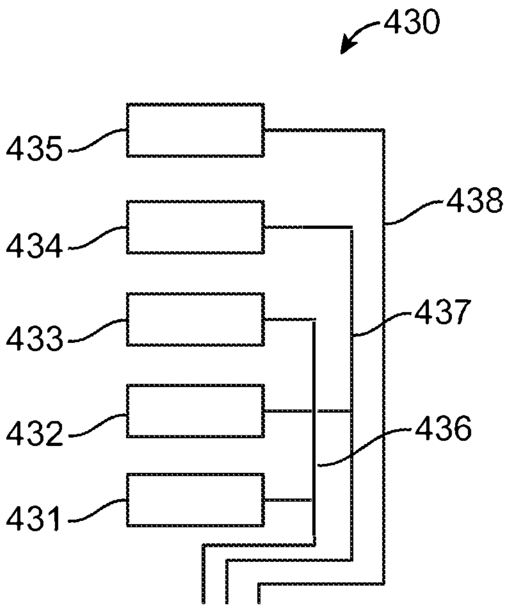

FIGS. 6E and 6F illustrate capacitive sensors having a plurality of discrete sensing regions configured to be placed along a length, such as the height, of the reservoir. A capacitive sensor may comprise an array 425 of uniformly-sized sensing regions 426, as shown in FIG. 6E, or the sensor may comprise an array 430 of discrete sensing regions 431-435, each having a different size, as shown in FIG. 6F. When fluid in the reservoir comes in proximity to or in contact with a discrete sensing region, a change in capacitance of the sensing region can be detected and recorded by the microprocessor. When the fluid level of the reservoir falls between two discrete regions, the sensors may detect very little or no changes in capacitance. Hence, the spacing between two adjacent discrete sensing regions can determine the resolution or detectable increment in the measurement of fluid volume, wherein smaller spacing can provide a finer resolution. The spacing may be adjusted so as to provide any desired resolution, for example 1 oz, ½ oz, ¼ oz, ⅛ oz, or 40 ml, 30 ml, 20 ml, 10 ml, or 5 ml. An array of discrete sensing regions may be configured to have constant or varying spacing between two adjacent sensing regions. While the embodiments of FIGS. 6E and 6F show rectangularly-shaped discrete sensing regions, a discrete sensing region may have any shape or size suitable for detecting changes in capacitance affected by the fluid inside the reservoir. Further, a capacitive sensor may comprise any number of discrete sensing regions, in any combination of shapes and sizes. In the embodiment of FIG. 6F, the discrete sensing regions are shown to increase in area from one end of the array 430 to the other, such that sensing region 431 has the smallest area, and sensing region 435 has the largest area. Such a configuration may help compensate for the saturation effects of the capacitive sensor as described in relation to the embodiments of FIGS. 6A and 6B.

Each sensing region may be connected to its own read-out channel in the microprocessor, via a separate, dedicated line, as shown in FIG. 6E. Alternatively or in combination, two or more sensing regions may be connected to a single read-out channel via the same line. For example, as shown in FIG. 6F, sensing regions 431 and 433 may be connected to line 436, regions 432 and 434 may be connected to line 437, and region 435 may be connected to line 438. In such a configuration, a read-out channel connected to two or more sensing regions may detect only half of the total capacitance change when only half of the connected sensing regions are in proximity to the fluid. Such a configuration can help simplify system configuration and reduce power requirements of the system, by reducing the number of required read-out channels.

Each discrete sensing region may be disposed on a known position along the height of the reservoir, such that the measurement data generated by the sensing regions can be used to determine the fluid level. For example, in the embodiment shown in FIG. 6F, the system may be programmed to know that sensing region 431 has a vertical position that is offset from the bottom of the reservoir by ⅕ of the total height of the reservoir. The system may further be programmed with a translation between fluid height and fluid volume for a specific operating state of the reservoir, such that the volume of the fluid in the reservoir may be calculated from the fluid levels as indicated by the sensors. Capacitive sensors comprising an array of discrete sensing regions can provide the advantage of reduced power consumption by the system, since the system can be configured to supply power to only a portion of the array of sensing regions. For example, in the embodiment of FIG. 6F, if sensing region 431 does not detect any fluid, the system may be configured to pause interrogation of sensing regions 432, 433, 434, and 435, thus conserving power.

The various shapes of the sensing regions shown in FIGS. 6A-6H may be combined in any way. For example, a capacitive sensor may comprise a plurality of continuous sensing regions having different shapes (e.g., multi-fingered and uniform), or a capacitive sensor may comprise a combination of a continuous sensing region and an array of discrete sensing regions. Further, one or more capacitive sensors having different configurations of sensing regions may be combined in a single fluid sensing unit.

Figure 6G:
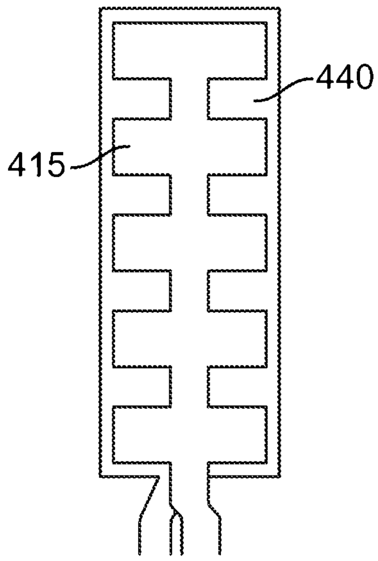
FIGS. 6G and 6H illustrate an exemplary embodiment of a base sensor that may be coupled to a capacitive sensor in accordance with embodiments.
Figure 6H:
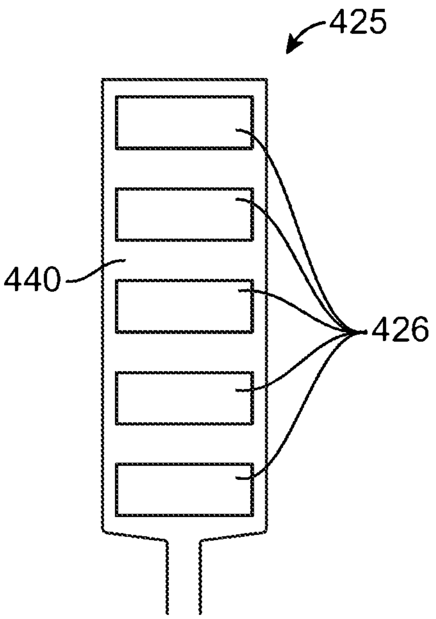

FIGS. 6G and 6H illustrate an exemplary embodiment of a base sensor 440 that may be coupled to a capacitive sensor in accordance with embodiments. The base sensor 440 may be optionally coupled to any capacitive sensor as described herein, such as the embodiments illustrated in FIGS. 6A-6F, in order to isolate the sensor from electrical interference. FIG. 6G shows the base sensor 440 coupled to a multi-fingered sensing region 415, while FIG. 6H shows the base sensor 440 coupled to an array 425 of discrete sensing regions 426. The base sensor can be disposed on the exterior side of the capacitive sensor, wherein the interior side of the sensor is oriented towards the interior surface of the reservoir, and can be held at a known voltage. In such a configuration, the base sensor may isolate the sensing regions of the capacitive sensors from interference from electrical and capacitive sources outside the reservoir (e.g., human fingers, water, milk, etc.).

Figure 7A:
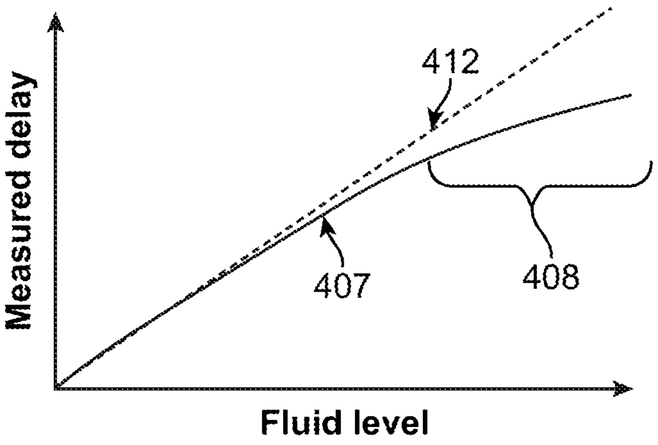
FIG. 7A is a graph showing an exemplary response of a continuous sensing region of a capacitive sensor.

FIG. 7A is a graph showing an exemplary response of a continuous sensing region of a capacitive sensor. In an ideal response 412, the increase in the fluid level (x-axis) is linearly related to an increase in the read-out value (measured time delay, y-axis). In such an ideal response, the continuous sensing region detects constantly increasing capacitance as the fluid level rises. A response 407 of a uniformly-shaped, continuous sensing region may differ from the ideal response 412. As the fluid level in the reservoir nears the maximal level, the concomitant increase in detected capacitance can begin to plateau (as shown by portion 408 of the response 407), as the capacitance of the sensing region reaches its saturation level. Accordingly, changes in fluid level near the capacity of the reservoir may become relatively more difficult to detect, when using continuous sensing regions having a uniform shape. A capacitive sensor having a continuous sensing region with a directionally varying shape, such as in the embodiment illustrated in FIG. 6B, may help to compensate for the saturation effect of the sensors, by increasing the capacitive area of the sensing region as the fluid level rises.

Figure 7B:
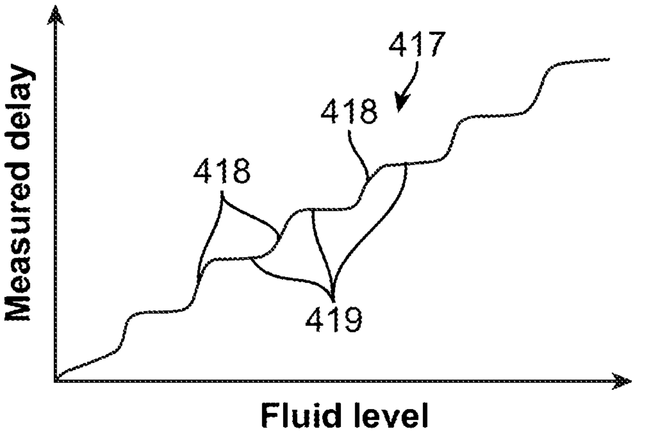
FIG. 7B is a graph showing an exemplary response of a continuous, multi-fingered sensing region of a capacitive sensor.

FIG. 7B is a graph showing an exemplary response 417 of a continuous, multi-fingered sensing region, such as in the embodiment illustrated in FIG. 6D. In the response 417 shown, as the fluid level rises, the read-out value (time delay) indicating the change in capacitance generally rises. Due to the non-uniform shape of the sensing regions, wherein a series of fingers having large capacitive areas are connected by stem portions having relatively smaller areas, the response 417 may not be completely linear. For example, small "bumps" 418 in the response may be detected, caused by large increases in the measured response as the fluid level rises to submerge a large capacitive area. The relatively smaller connecting areas between the large areas may contribute a relatively smaller amount of change in capacitance, shown by the relatively flatter portions 419 of the response 417. The "bumps" or relatively steeper portions 418 of the response may facilitate the determination of the correct fluid level from the measurement data, by providing clearly-identifiable points in the response that can be correlated to known positions of specific areas of a sensing region along the length of the reservoir.

Figure 7C:
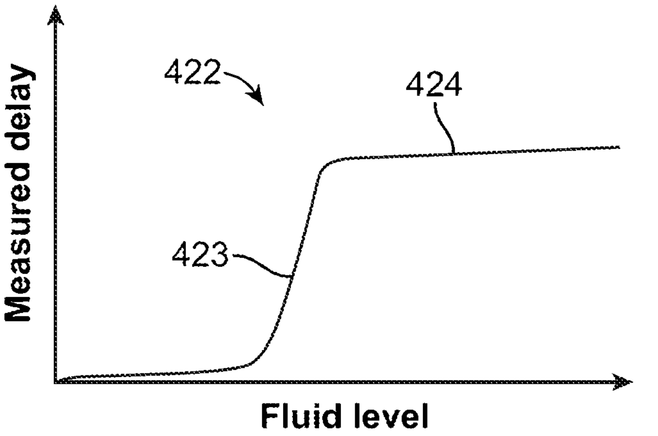
FIG. 7C is a graph showing an exemplary response of a discrete sensing region of a capacitive sensor.

FIG. 7C is a graph showing an exemplary response 422 of a discrete sensing region, such as in the embodiments illustrated in FIGS. 6E and 6F. A single discrete sensing region will generally remain substantially unresponsive until the fluid level rises sufficiently to come in proximity to or in contact with the sensing region. Once fluid is in proximity to or in contact with the sensing region, the sensing region may detect a large increase in capacitance that continues to increase as the fluid level rises over the height of the sensing region, as shown by portion 423 of the response 422. When the fluid level rises above the sensing region to fully cover the entire sensing region, the capacitance of the sensing region can reach its saturation level, resulting in a plateau 424 in the measured response of the sensing region. In this manner, a capacitive sensor comprising a plurality of discrete sensing regions can clearly identify the points at which the fluid level rises to the position of each discrete sensing region along the length of the reservoir, thereby facilitating the determination of fluid level as well as enabling the determination of the orientation or tilt of the reservoir.

The measurement data generated by the one or more capacitive sensors may be transmitted to a processing unit, as described herein. The processing unit may further receive measurement data generated by one or more reservoir sensors, configured to measure a position, orientation, or motion of the reservoir, and/or by one or more proximity sensors, configured to detect the connection of the reservoir to another component such as a pumping device or a feeding attachment. The collective measurement data, including data generated by the fluid sensing unit as well as data generated by the reservoir sensors, may subsequently be analyzed in order to determine the volume of fluid contained in the reservoir. The analysis may be performed by the microprocessor of the processing unit integrated with the sensing reservoir, or by another computing device in communication with the processing unit. For example, the analysis may be performed by a personal computing device (e.g., smartphone, tablet, laptop), or by a remote server in communication with the personal computing device and/or the sensing reservoir. Alternatively, the analysis may be performed partially by the processing unit of the sensing reservoir, and partially by another computing device.

The measurement data generated by one or more capacitive sensors as described herein may be analyzed using an algorithm appropriately selected for the specific configuration of the capacitive sensor's sensing regions. In many embodiments, the algorithms include a calibration step, wherein a translation may be established between the read-out values of a particular sensor and the corresponding fluid level. The translation may be stored in a memory of the processing unit performing the analysis.

For sensors comprising continuous sensing regions, the algorithm may comprise an initial calibration to determine 1) a reference or baseline value, corresponding to the sensor response when there is no fluid in the reservoir, and 2) a maximum fill value, corresponding to the sensor response when the reservoir is filled to the maximal level. The sensor response value for a specific measurement may then be compared to the reference value and the maximum fill value, to determine the proportion of the maximum fill value represented by the measured value.

For sensors comprising continuous sensing regions with non-uniform shapes, such as the multi-fingered configurations illustrated in FIGS. 6C and 6D, the periodic jumps in detected capacitance, corresponding to the fluid level reaching the relatively large capacitive areas of a sensing region, can enable the determination of fluid level for a specific sensor measurement. For example, the measured sensor response can be divided by a constant value representing the sensor response for a single large capacitive area, and a marginal response value can be added to account for the sensor response for the relatively smaller, connective area. Fluid levels corresponding to the sensor response values may be determined using known positions of the sensing region's capacitive areas along the length of the reservoir.

For sensors comprising a plurality of discrete sensing regions, the measured response of each sensing region may be compared against a baseline value determined during an initial calibration. When the measured response of a specific sensing region is close to or exceeds its baseline value, the fluid level can be determined to have reached the location of the specific sensing region. To determine the fluid level of a sensor comprising an array of discrete sensing regions, the read-out values of the sensing regions may be processed starting from the sensing region at the lowest position in the array; information generated by the reservoir sensors may be used to determine which sensing region is at the lowest position, based on the orientation or operating state (upright/filling or inverted/draining) of the sensing reservoir. When multiple sensing regions are connected to a single read-out channel, a combination of processing techniques can be used to determine the fluid level.

Figure 8A:
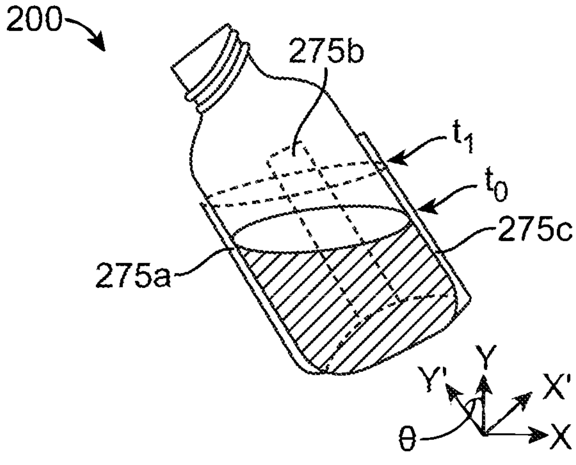
FIG. 8A illustrates an exemplary embodiment of a sensing reservoir in the filling state, in a tilted orientation.

FIG. 8A illustrates an exemplary embodiment of a sensing reservoir 200 in the filling state, at a tilted orientation. The reservoir comprises a plurality of fluid sensors 275*a*, 275*b*, and 275*c*, dispersed about the periphery of the reservoir. While FIG. 8A shows the fluid sensors 275*a* and 275*b*, and sensors 275*b* and 275*c* rotationally offset from each other at 90° angles, and sensors 275*a* and 275*c* rotationally offset from each other at a 180° angle, the sensors may be distributed in any predetermined distribution that enables the determination of the reservoir's orientation. Generally, an equal distribution of the plurality of fluid sensors about the periphery of the reservoir can yield the most accurate estimation of the reservoir's orientation. As described herein, the read-out value of each fluid sensor can be processed to indicate the fluid level at the specific sensor. The fluid level at the three locations of the fluid sensors can be triangulated to determine the angle θ, corresponding to the tilt or vertical offset of the reservoir with respect to a vertical position. The known tilt or orientation of the reservoir can then allow the calculation of fluid volume based on the fluid levels at the three fluid sensors.

Figure 8B:
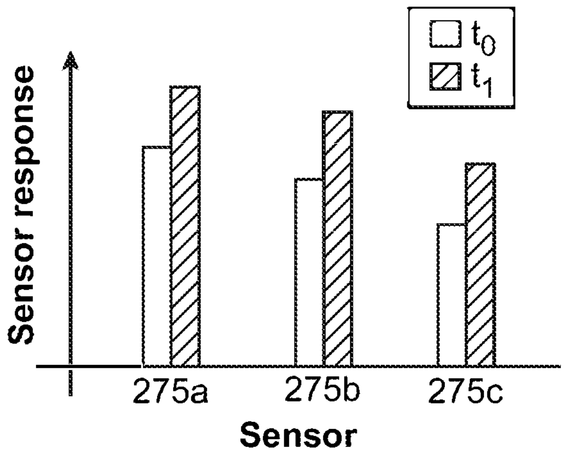
FIGS. 8B and 8C show exemplary graphs of fluid sensor response measured during operation of the sensing reservoir of FIG. 8A, in the filling state.
Figure 8C:
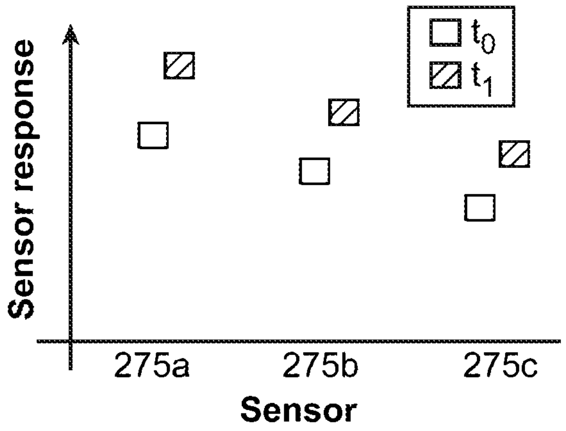

FIGS. 8B and 8C show exemplary graphs of fluid sensor response measured during operation of a sensing reservoir of FIG. 8A, in the filling state. FIG. 8B represents exemplary measurement data generated by fluid sensors having continuous sensing regions, and FIG. 8C represents exemplary measurement data generated by fluid sensors having a plurality of discrete sensing regions. The graphs of FIGS. 8A and 8B indicate sensor response measured at an initial time point, $t_0$, and at a subsequent time point, $t_1$, wherein the fluid level at $t_1$ is higher than the fluid level at $t_0$ for a reservoir in the filling state. Depending on the tilt or orientation of the reservoir, the plurality of fluid sensors may report different read-out values. For example, in the reservoir shown in FIG.

8A, sensor 275*a* reports the highest read-out value of the three sensors, due to the tilt or vertical offset angle θ of the reservoir. For a sensing reservoir in a perfectly vertical position (e.g., angle θ equals 0), the plurality of fluid sensors can report the same read-out values. Thus, the fluid levels measured at different sensor locations can help determine the orientation of the reservoir.

Figure 9A:
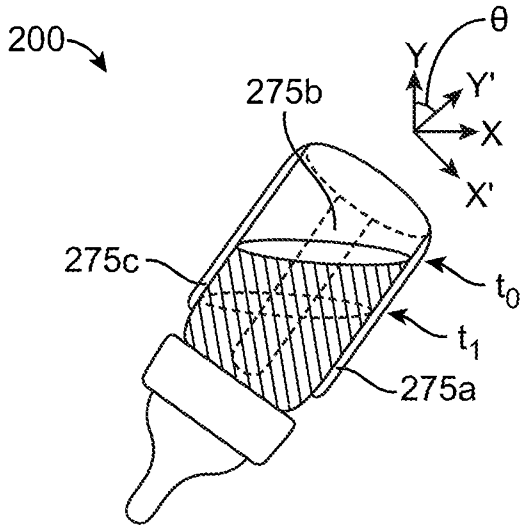
FIG. 9A illustrates an exemplary embodiment of a sensing reservoir in the draining state, at a tilted orientation.

FIG. 9A illustrates an exemplary embodiment of a sensing reservoir 200 in the draining state, at a tilted orientation. In the draining state, the reservoir may be coupled to a feeding nipple as shown, so as to feed the milk contained in the reservoir to an infant. The reservoir comprises a plurality of fluid sensors 275*a*, 275*b*, and 275*c*, dispersed about the periphery of the reservoir. As described herein, the read-out value of each fluid sensor can be processed to indicate the fluid level at the specific sensor. The fluid level at the three locations of the fluid sensors can be triangulated to determine the angle θ, corresponding to the tilt or vertical offset of the reservoir with respect to a vertical position. The known tilt or orientation of the reservoir can then allow the calculation of fluid volume based on the fluid levels at the three fluid sensors.

Figure 9B:
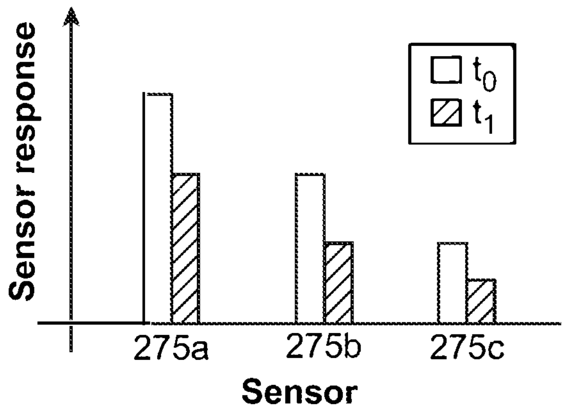
FIGS. 9B and 9C show exemplary graphs of fluid sensor response measured during operation of the sensing reservoir of FIG. 9A, in the draining state.
Figure 9C:
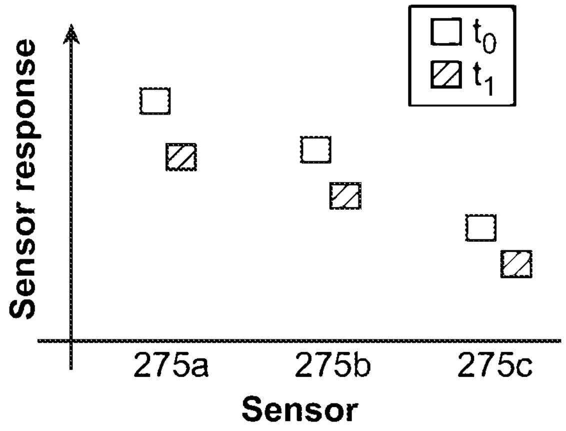

FIGS. 9B and 9C show exemplary graphs of fluid sensor response measured during operation of a sensing reservoir of FIG. 9A, in the draining state. FIG. 9B represents exemplary measurement data generated by fluid sensors having continuous sensing regions, and FIG. 9C represents exemplary measurement data generated by fluid sensors having a plurality of discrete sensing regions. The graphs of FIGS. 9A and 9B indicate sensor response measured at an initial time point, $t_0$, and at a subsequent time point, $t_1$, wherein the fluid level at $t_1$ is lower than the fluid level at $t_0$ for a reservoir in the draining state. Depending on the tilt or orientation of the reservoir, the plurality of fluid sensors may report different read-out values. For example, in the reservoir shown in FIG. 9A, sensor 275*a* reports the highest read-out value of the three sensors, due to the tilt angle 315 of the reservoir. For a sensing reservoir in a perfectly vertical position (e.g., angle θ equals 0), the plurality of fluid sensors can report the same read-out values. Thus, the fluid levels measured at different sensor locations can help determine the orientation of the reservoir.

While the vertical tilt of the reservoir may be determined from the fluid sensor data, the operating state of the reservoir (filling or draining) may be difficult to establish based only on the fluid sensor data. Whether the fluid sensors comprise continuous sensing regions or a plurality of discrete sensing regions, the generated measurement signals may be similar for reservoirs in an upright position (filling state) or in an inverted position (draining state). The translation between sensor response and fluid levels, and hence fluid volume, can differ depending on the operating state of the reservoir, since the geometry of the top of the reservoir may differ from the geometry of the bottom of the reservoir. In order to accurately determine fluid levels from measured sensor response, one or more reservoir sensors configured to determine an orientation or motion of the reservoir may be provided with the sensing reservoir. For example, one or more gyroscopes and/or accelerometers may be provided to sense the motion and orientation of the reservoir, thereby enabling the sensing reservoir to toggle the operating state of the system between filling and draining. The reservoir sensors can also help to eliminate noisy readings, by detecting excessive motion and thereby giving the system an indication to pause data collection until the reservoir reaches a more stable state.

In embodiments of the sensing reservoir further comprising one or more proximity sensors, measurement data from the proximity sensors may also be used to determine the orientation and corresponding operating state of the sensing reservoir. For example, as described herein, a proximity sensor may detect the coupling of the reservoir to a pumping device, which may indicate that the reservoir is in a generally upright orientation and about to begin filling with fluid. A proximity sensor may detect the coupling of the reservoir to a feeding attachment, which may indicate that the reservoir is in a generally inverted orientation and about to begin draining. The information provided by the proximity sensors can not only be used to efficiently manage the data measurement by the fluid sensing unit, as described further herein, but can also provide validation of the tilt or orientation of the reservoir as determined by measurement data from the reservoir sensors and/or the fluid sensing unit.

Figure 10:
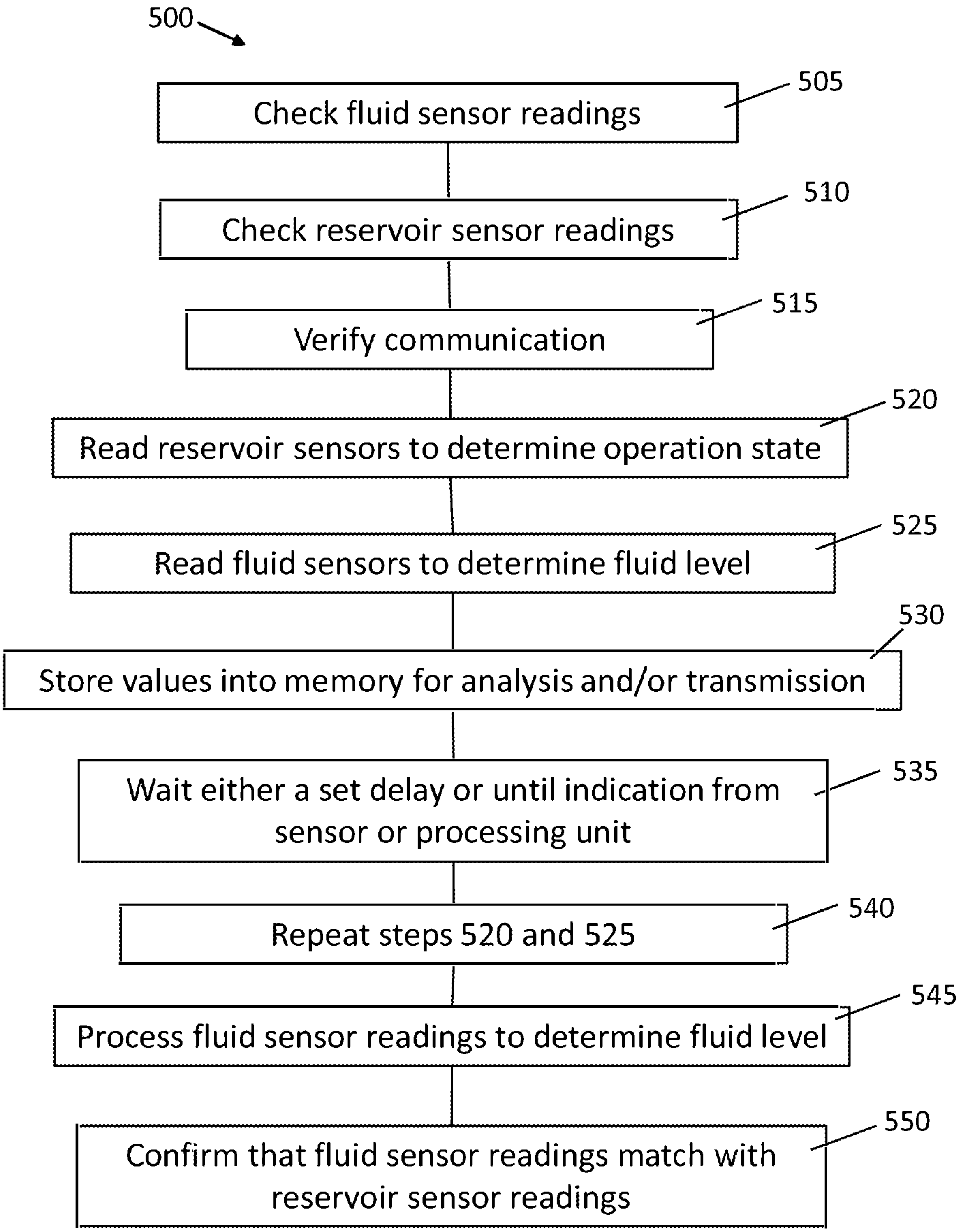
FIG. 10 illustrates an exemplary method for determining the volume of fluid contained in a sensing reservoir in accordance with embodiments.

FIG. 10 illustrates a method 500 for determining the volume of fluid contained in a sensing reservoir in accordance with embodiments. The method 500 may comprise three stages: 1) system setup; 2) measurement data generation; and 3) data analysis.

System setup may comprise steps 505-515. At step 505, fluid sensor readings are taken to check that the fluid sensors are working properly. For example, a baseline read-out value of the fluid sensors may be compared to a known baseline value, to ensure that the readings fall within an appropriate range. At step 510, reservoir sensor readings are taken to check that the motion or tilt readings fall within an appropriate range. For example, accelerometer readings may be taken to ensure that the reservoir is not undergoing excessive motion. At step 515, the communication between the sensors and the processing unit may be verified.

Measurement data generation may comprise steps 520-540. At step 520, the reservoir sensors may be read to determine the operating state of the sensing reservoir (e.g., filling state or draining state). At step 525, the fluid sensors may be read to generate read-out values indicative of the level of fluid at each fluid sensor. At step 530, the read-out values generated by the fluid sensors and/or the reservoir sensors may be stored into a memory of the processing unit, for storage and/or transmission to another computing device. At step 535, the system may wait a set delay, or wait until an indication to continue is received from the sensing unit or the processing unit. At step 540, the sensor reading steps 520 and 525*a* re repeated. Steps 520-540 of measurement data generation may be repeated continuously as long as motion of the sensing reservoir is detected, or a change over time in the read-out values of the fluid sensors is detected. When neither motion of the reservoir nor changes in the fluid sensor readings are detected, the sensing reservoir may enter an inactive or "sleep" state, during which the generation of measurement data may be paused.

Data analysis may comprise steps 545-550. At step 545, the fluid sensor readings may be processed in order to determine fluid level values. If the fluid sensors comprise continuous sensing regions, the sensor read-out at each measurement may be used to determine the fluid level. If the fluid sensors comprise a plurality of discrete sensing regions, the orientation of the reservoir (upright or inverted) as determined by the reservoir sensor readings may be used to determine which sensing region is at the lowest position, and the fluid sensor data from the plurality of regions may be processed sequentially from the sensing region at the lowest position through to the sensing region at the highest position. At step 550, the processed fluid sensor data may be compared with the reservoir sensor readings in order to ensure that the two sets of data generally match.

The steps of method 500 are provided as an example of a method to determine a fluid volume using a sensing reservoir, in accordance with embodiments. A person of ordinary skill in the art will recognize many variations and modifications based on the disclosure provided herein. For example, some steps may be added or removed. Some of the steps may comprise sub-steps, and many of the steps may be repeated. The processor as described herein can be programmed with one or more instructions to perform one or more of the steps of method 500.

Referring again to FIGS. 3A-4C, in some embodiments, a sensing reservoir 300 may comprise a fluid sensing unit 370 having only a single fluid sensor 375. In such a configuration, the triangulation of the fluid levels to determine the orientation of the reservoir, as shown and described with reference to FIGS. 8A-9C, may not be possible. To determine the orientation and the corresponding operating state of the sensing reservoir (e.g., upright/filling, inverted/draining), measurement data from the one or more reservoir sensors, such as accelerometers and/or gyroscopes, may be analyzed. Alternatively or in combination, data from the proximity sensors may also be used to confirm the orientation and corresponding operating state of the sensing reservoir as determined by the reservoir sensors.

Figures 11A, 11B, 11C, 11D, 11E, 11F:
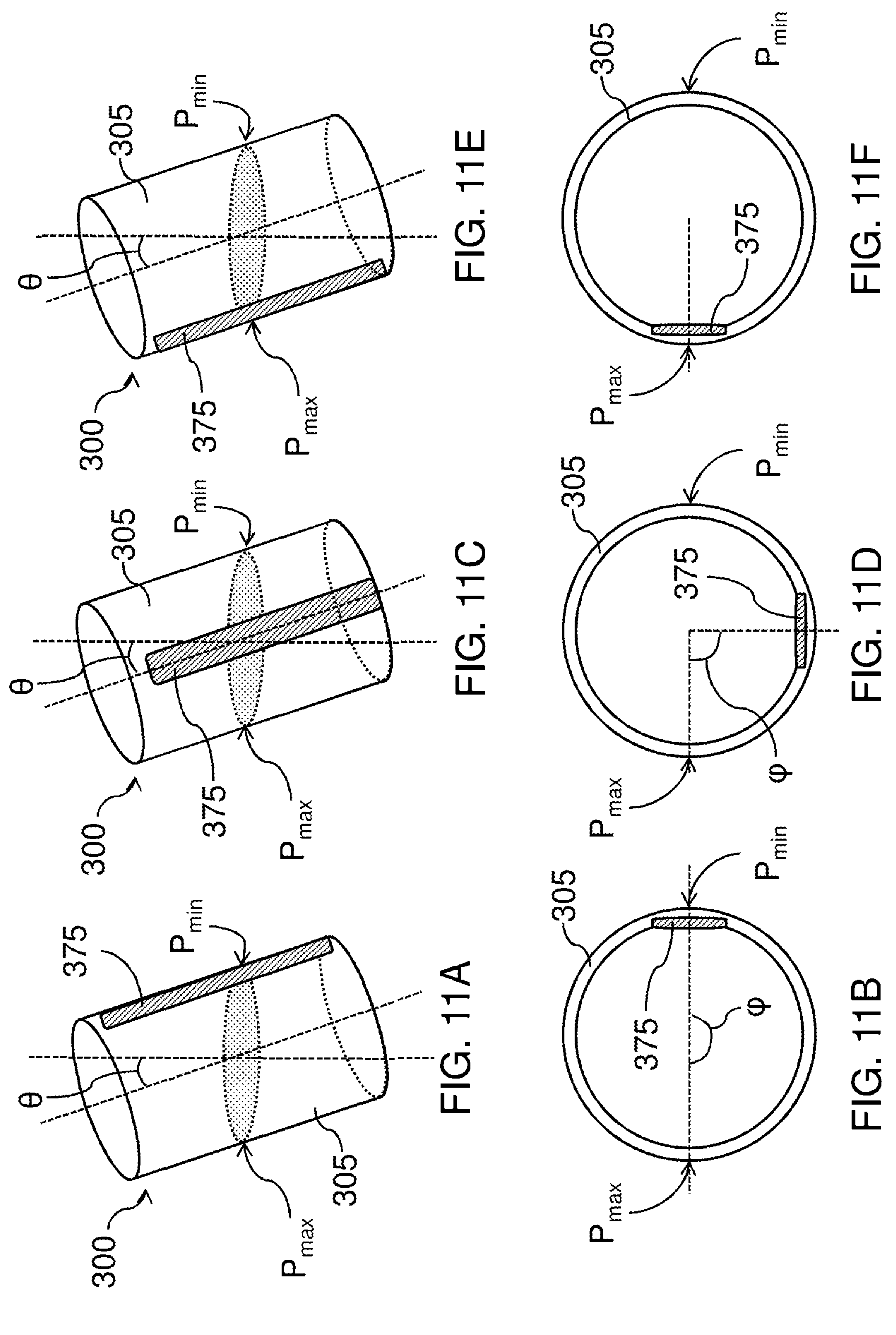
FIGS. 11A and 11B show a side perspective view and a top view, respectively, of a sensing reservoir comprising a single fluid sensor, oriented at a maximum rotational offset.
FIGS. 11C and 11D show a side perspective view and a top view, respectively, of a sensing reservoir comprising a single fluid sensor, oriented at an intermediate rotational offset.
FIGS. 11E and 11F show a side perspective view and a top view, respectively, of a sensing reservoir comprising a single fluid sensor, oriented at zero rotational offset.

In embodiments of the sensing reservoir comprising a single fluid sensor, the tilt or vertical offset of the reservoir as well as the rotational offset of the reservoir can affect the accuracy of fluid level measurement by the fluid sensor. FIGS. 11A and 11B show a side perspective view and a top view, respectively, of a sensing reservoir 300 comprising a single fluid sensor 375, oriented at a maximum rotational offset. The sensing reservoir is shown tilted, or vertically offset by an angle θ with respect to the vertical axis of the reservoir in a fully upright position. At this vertical offset, the fluid level is highest at point $P_{max}$ along the periphery of the reservoir, positioned at the base of the tilt. Conversely, the fluid level is lowest at point $P_{min}$ directly opposite point $P_{max}$. As shown in FIG. 11B, the fluid sensor 375 is rotationally offset from point $P_{max}$ by an angle φ of 180°. At this maximum rotational offset, the fluid sensor is positioned over point $P_{min}$, at which the fluid level is lowest. Therefore, at this maximum rotational offset of the fluid sensor with respect to the base of the tilt, the measurement generated by the fluid sensor is generally less reliable. FIGS. 11C and 11D show a side perspective view and a top view, respectively, of a sensing reservoir 300 comprising a single fluid sensor 375, oriented at an intermediate rotational offset. As in FIGS. 11A and 11B, the sensing reservoir is shown tilted, or vertically offset by an angle θ with respect to the vertical axis of the reservoir in a fully upright position. As shown in FIG. 11D, however, the fluid sensor 375 is now rotationally offset from point $P_{max}$ by an angle φ of 90° rather than 180°. In this orientation, the fluid sensor can generate a measurement with higher confidence than in the orientation shown in FIGS. 11A and 11B. FIGS. 11E and 11F show a side perspective view and a top view, respectively, of a sensing reservoir 300 comprising a single fluid sensor 375, oriented at zero rotational offset. As in FIGS. 11A-11D, the sensing reservoir is shown tilted, or vertically offset by an angle θ with respect to the vertical axis of the reservoir in a fully upright position. As shown in FIG. 11F, however, the fluid sensor 375 is now positioned over point $P_{max}$, or at a rotational offset angle φ of 0°. In this orientation, the fluid sensor can generate a measurement with maximum confidence for the given vertical offset.

Figure 12:
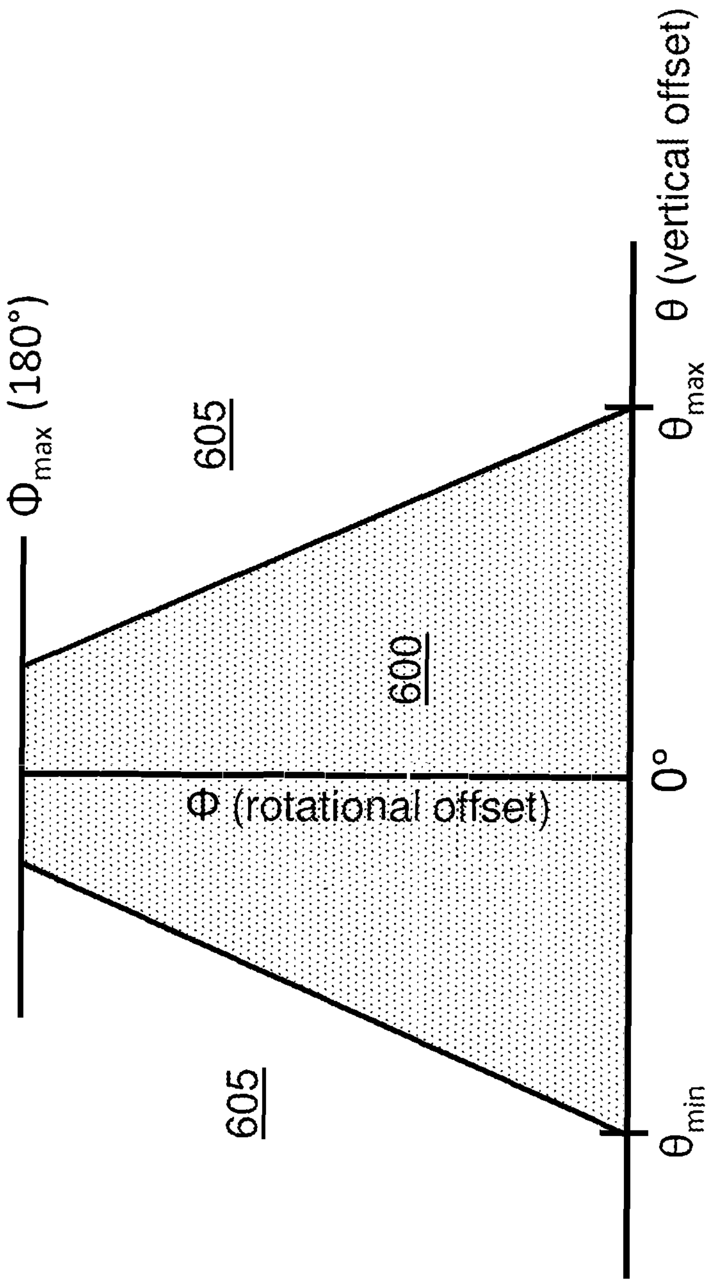
FIG. 12 illustrates the effect of vertical and rotational offset of a sensing reservoir on the confidence of measurement data generated by a fluid sensing unit of the reservoir.

FIG. 12 illustrates the effect of vertical and rotational offset of a sensing reservoir on the confidence of measurement data generated by a fluid sensing unit of the reservoir. The x-axis represents the tilt or vertical offset of the reservoir with respect to the upright position, in terms of angle θ. The y-axis represents the rotational offset of the fluid sensor with respect to the position along the periphery of the reservoir at the base of the tilt, in terms of angle φ. As described with reference to FIGS. 11A-11F, the rotational offset φ can range from a minimum of 0° (bottom horizontal line/x-axis) to a maximum of 180° (top horizontal line). For vertical and rotational offsets falling within the shaded area 600, the fluid sensing unit provides relatively high-confidence measurements, whereas for vertical and rotational offsets falling outside of the shaded area 605, the fluid sensing unit provides relatively low confidence measurements. As shown in this graph, the greater the rotational offset, the smaller the allowable vertical offset that could still yield relatively high-confidence measurements by the fluid sensing unit. Conversely, the greater the vertical offset, the smaller the allowable rotation offset that could still yield relatively high-confidence measurements by the fluid sensing unit.

In order to improve the efficiency and accuracy of fluid level measurements by the sensing reservoir, the processing unit may be configured to determine whether the reservoir is in an acceptable orientation for fluid measurement, prior to interrogating the fluid sensors for measurement data. Acceptable ranges of vertical and rotational offsets may be calculated based on the specific dimensions and/or characteristics of the sensing reservoir and its components. When the sensing reservoir is determined to be oriented outside of the predetermined acceptable ranges of vertical and rotational offsets, the processing unit may forgo interrogation of the fluid sensors for fluid level measurement, in view of the high probability that the measurement may yield unusable data. Data collection by the fluid sensing unit may be paused until the reservoir is determined to be oriented within the acceptable ranges of vertical and rotational offsets. Such a system configuration can help reduce or eliminate noisy fluid sensor readings, as well as improve the efficiency of power consumption by the system.

Figure 13:
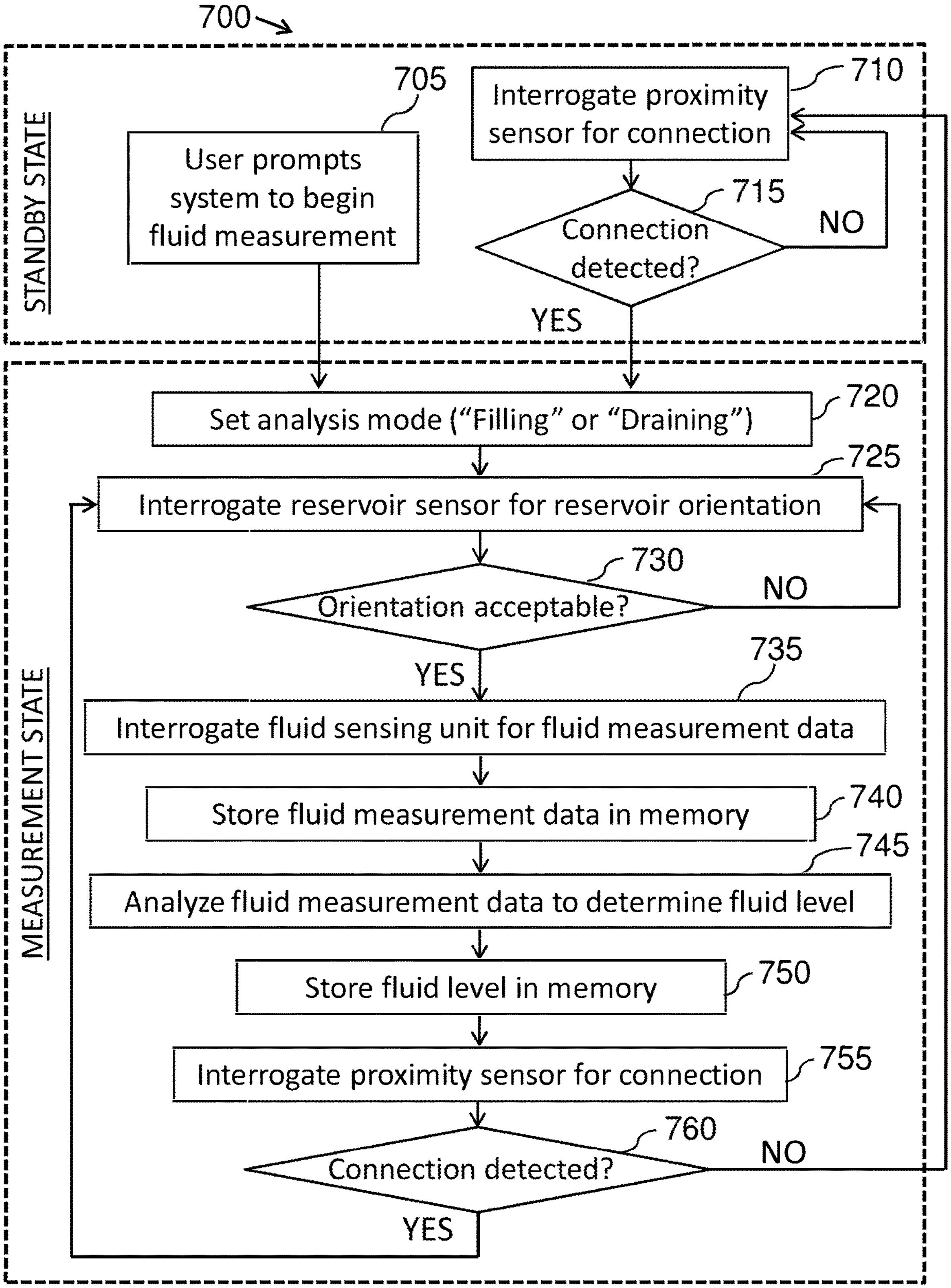
FIG. 13 illustrates a method for determining the volume of fluid contained in a sensing reservoir in accordance with embodiments.

FIG. 13 illustrates a method 700 for determining the volume of fluid contained in a sensing reservoir in accordance with embodiments. Method 700 comprises switching between a low-power, standby state and a measurement state based on information provided by one or more proximity sensors (e.g., LED/photodiode assemblies, Hall effect sensors, reed switches) of the sensing reservoir. Steps 705-710 may be performed while the sensing reservoir is operating in a low-power, standby state, wherein the reservoir is not measuring fluid levels. Steps 715-755 may be performed while the sensing reservoir is operation in a measurement state, wherein the reservoir is actively measuring fluid levels.

At step 705, a user of the sensing reservoir may prompt the system to begin fluid measurement. For example, the user may indicate through a user interface of the sensing reservoir (e.g., mobile application) or using a physical switch or button on the reservoir that the user is about to begin pumping or feeding, thereby that the reservoir is about to begin filling or draining. At step 710, the processing unit may interrogate the proximity sensor to determine whether a connection to another component (e.g., pumping device, feeding attachment) is detected. The processing unit may be configured to perform step 705 at regular, pre-set intervals, for example every 1 second. At step 715, the processing unit may determine whether a connection is detected, based on data from the proximity sensor. If a connection is not detected, step 705 may be repeated.

If a connection is detected, at step 715, the processing unit may set the analysis mode to "filling" or "draining" based on the detected component type. For example, if the proximity sensor detects a connection to a pumping device, the analysis mode may be set to "filling". If the proximity sensor detects a connection to a feeding attachment, the analysis mode may be set to "draining".

At step 720, the processing unit may interrogate one or more reservoir sensors (e.g., accelerometers and/or gyroscopes) for reservoir orientation information. For example, the reservoir sensors can provide the vertical offset and rotational offset of the reservoir as described herein. At step 725, the processing unit may determine whether the orientation of the sensing reservoir is acceptable for fluid measurement. As described herein, the processing unit may be pre-programmed with acceptable ranges or threshold values for vertical and rotational offset of the reservoir, against which the measured values may be compared. If the orientation is found to be unacceptable for fluid measurement (e.g., confidence of fluid measurement data would be low at given orientation), step 720 may be repeated at regular, pre-set intervals (e.g., every 1 second) until an acceptable orientation is detected.

If the orientation is found to be acceptable, at step 730, the processing unit may interrogate the fluid sensing unit to obtain fluid measurement data. At step 735, the measurement data may be stored in a memory of the processing unit. At step 740, the processing unit may analyze the fluid measurement data to determine fluid level of the milk contained within the reservoir. At step 745, the determined fluid level data may be stored in the memory.

At step 750, the processing unit may interrogate the proximity sensor again to determine whether the connection to the component is still detected. At step 755, the processing unit may determine whether or not the connection is still detected, based on data from the proximity sensor. If the connection is still connected, steps 720-755 may be repeated. If the connection is no longer detected, the sensing reservoir may return to the low-power, standby state, and step 705 may be repeated.

The steps of method 700 are provided as an example of a method to determine a fluid volume using a sensing reservoir, in accordance with embodiments. A person of ordinary skill in the art will recognize many variations and modifications based on the disclosure provided herein. For example, some steps may be added or removed. Some of the steps may comprise sub-steps, and many of the steps may be repeated. The processor as described herein can be programmed with one or more instructions to perform one or more of the steps of method 700.

Figure 14:
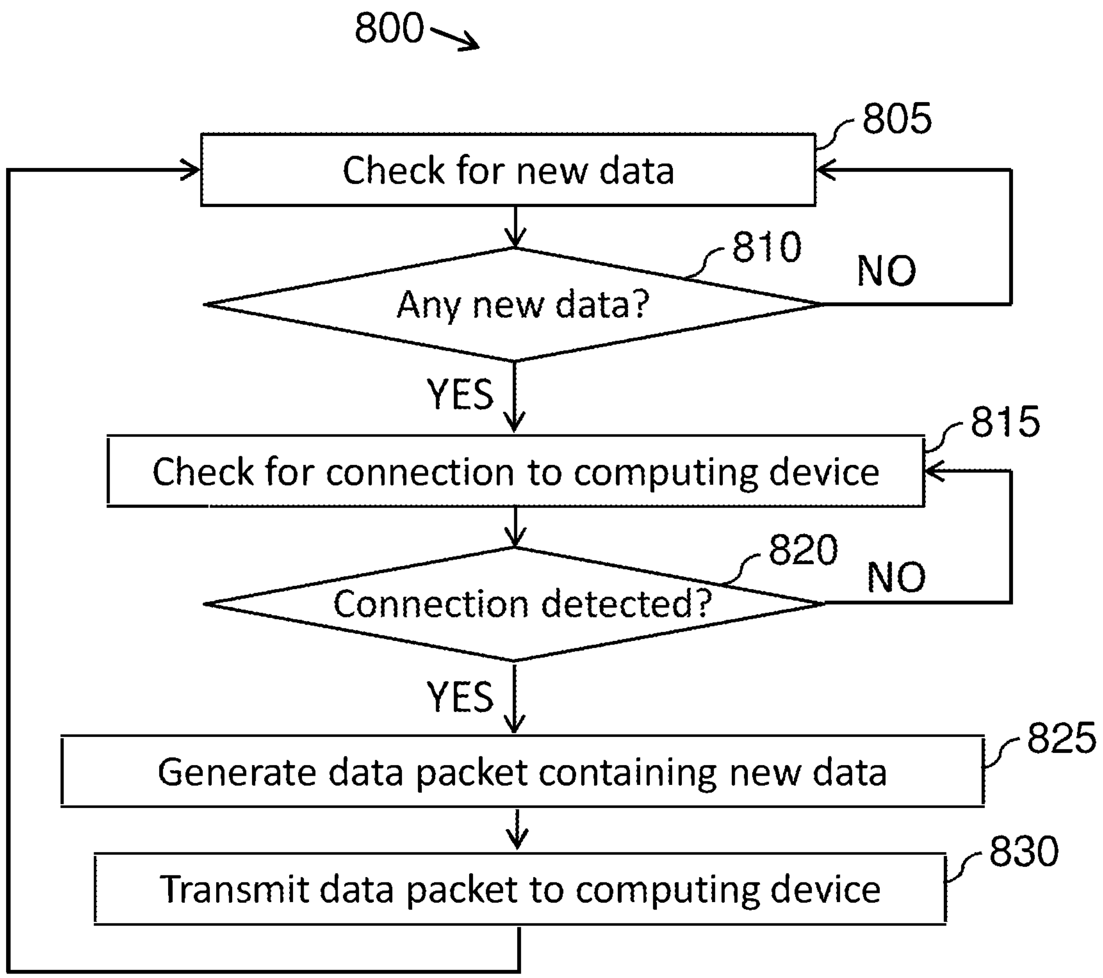
FIG. 14 illustrates a method for transmitting data from a sensing reservoir in accordance with embodiments.

FIG. 14 illustrates a method 800 for transmitting data from a sensing reservoir in accordance with embodiments. The steps of the method 800 may be repeated at regular, pre-set intervals (e.g., every 24 hours, every hour, every minute, etc.), or may be performed upon prompting by a user of the sensing reservoir.

At step 805, the processing unit of the sensing reservoir may check to see whether any new, not yet transmitted data is stored on the memory. At step 810, the processing unit determines whether there is new data to be transmitted. If not, step 805 may be repeated, for example at regular, pre-set intervals (e.g., every 24 hours, every hour, every minute, etc.).

If there is new data stored on the memory, at step 815, the processing unit may check for a connection to the computing device to which the user desires to transfer the data. The computing device may comprise a personal computer, laptop, tablet, or smartphone, which may be configured to provide a software or application to manage breast milk inventory. Alternatively or in combination, the computing device may comprise a remote server configured to store the user's data. Step 815 may be performed by a communication module coupled to or integrated with the processing unit, wherein the connection may comprise a wired connection, a wireless short range connection, or a wireless long range connection. At step 820, the processing unit determines whether connection is detected. If not, step 815 may be repeated, for example at regular, pre-set intervals.

If a connection to the computing device is detected, at step 825, the processing unit may generate a data packet containing all of the new data that has not yet been transmitted from the sensing reservoir. At step 830, the processing unit may transmit the data packet to the target computing device, for example via the communication module.

The steps of method 800 are provided as an example of a method to transmit measurement data from a sensing reservoir, in accordance with embodiments. A person of ordinary skill in the art will recognize many variations and modifications based on the disclosure provided herein. For example, some steps may be added or removed. Some of the steps may comprise sub-steps, and many of the steps may be repeated. The processor as described herein can be programmed with one or more instructions to perform one or more of the steps of method 800.

In any of the embodiments disclosed herein, the sensing reservoirs described herein can be configured to communicate with another entity, such as one or more computing devices and/or servers. Exemplary computing devices include personal computers, laptops, tablets, and mobile devices (e.g., smartphones, cellular phones). The servers can be implemented across physical hardware, virtualized computing resources (e.g., virtual machines), or any suitable combination thereof. For example, the servers may comprise distributed computing servers (also known as cloud servers) utilizing any suitable combination of public and/or private distributed computing resources. The computing devices and/or servers may be in close proximity to the sensing adaptor and the pumping device (short range communication), or may be situated remotely from the sensing adaptor and the pumping device (long range communication). Any description herein relating to communication between a computing device and a sensing reservoir can also be applied to communication between a server and a sensing reservoir, and vice-versa.

The sensing reservoir can communicate with another computing device via a communication module, as described herein. The communication module can utilize any communication method suitable for transmitting data, such as a wired communication (e.g., wires, cables such as USB cables, fiber optics) and/or wireless communication (Bluetooth®, WiFi, near field communication). In many embodiments, data can be transmitted over one or more networks, such as local area networks (LANs), wide area networks (WANs), telecommunications networks, the Internet, or suitable combinations thereof.

The computing device may be associated with data stores for storage of the measurement data and/or analysis results. Applications of the computing device can also collect and aggregate the measurement data and/or analysis results and display them in a suitable format to a user (e.g., charts, tables, graphs, images, etc.). Preferably, the application includes additional features that allow the user to overlay information such as lifestyle choices, diet, and strategies for increasing milk production, in order to facilitate the comparison of such information with milk production statistics. The analysis and display functionalities described herein may be performed by a single entity, or by any suitable combination of entities. For example, in many embodiments, data analysis can be carried out by a server, and the analysis results may be transmitted to another computing device for display to the user.

Other types of data can also be transmitted between the sensing adaptor and other computing devices. For example, in many embodiments, firmware updates for one or more components of the sensing adaptor can be transmitted to the adaptor from the computing device.

Figures 15A, 15B, 15C:
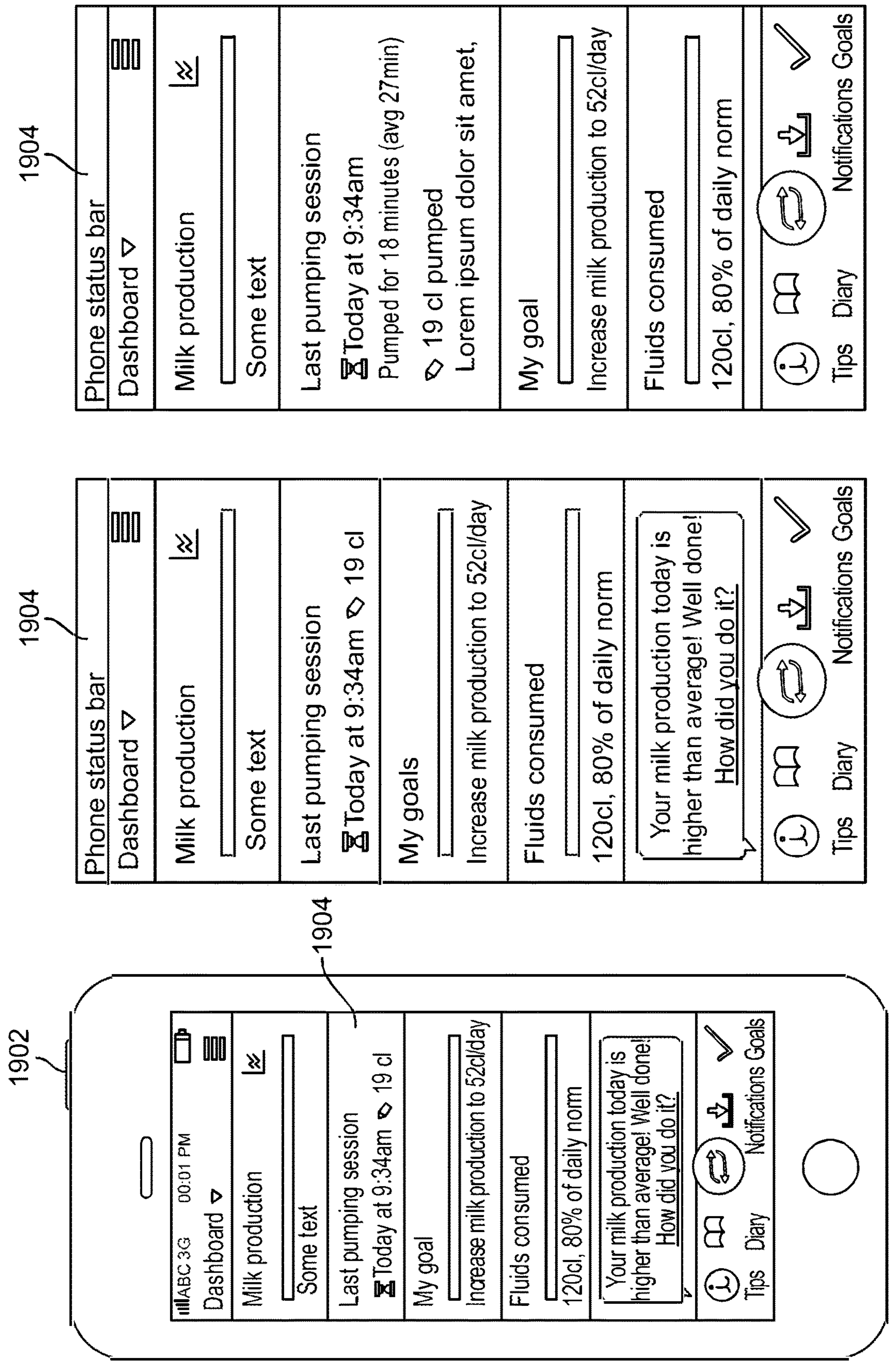
FIGS. 15A-15C illustrate exemplary computing device displays.

FIGS. 15A-15C illustrate exemplary computing device displays 1904. For example, FIG. 15A illustrates an exemplary display on a mobile phone 1902 and graphically illustrates milk production, the time of the last pumping session, a graphic of goal attainment, and a graphic illustrating the fluid consumption of the user. Additionally, the display 1904 may also provide user encouragement or user feedback based on the amount of milk production. FIG. 15B is an enlarged view of the display 1904 in FIG. 15A. FIG. 15C illustrates additional information that the display 1904 may show when a touch screen is actuated (e.g. by swiping or touching the screen). For example, the volume of the milk expressed is indicated after the "Last Pumping Session" section of the display is selected. Some or all items may be expanded, as also indicated in FIG. 15C. Additional information, or in some situations, less information may be displayed as desired.

Figure 16B:
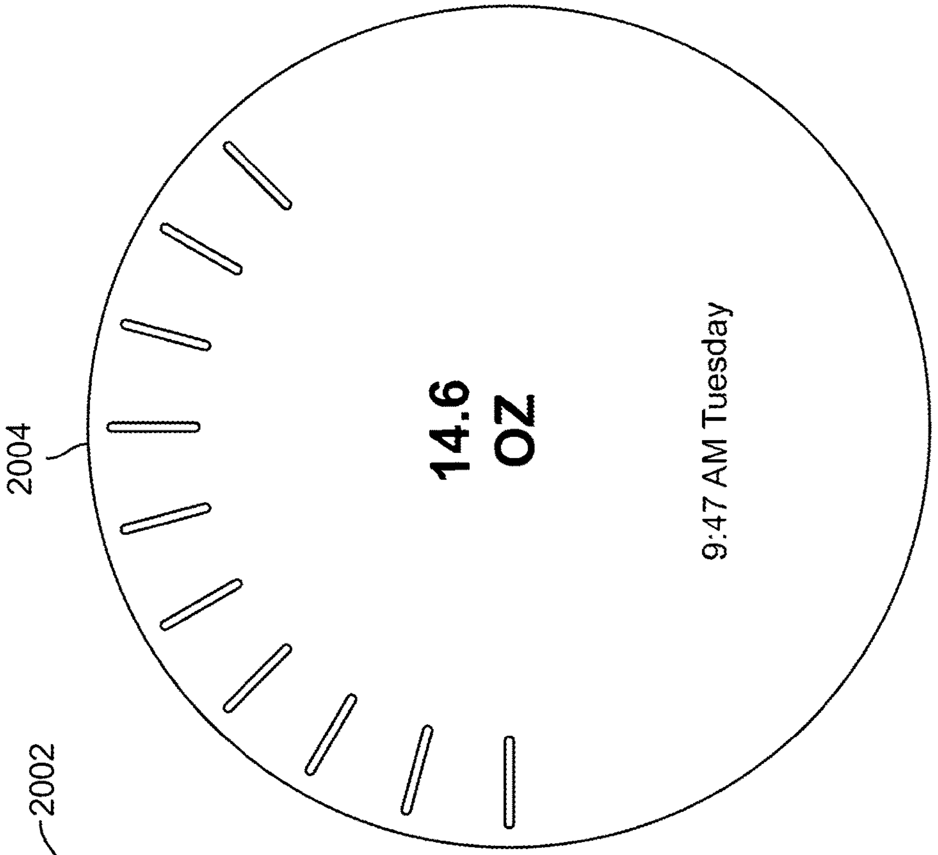
FIGS. 16A-16B illustrate other exemplary displays suitable for incorporation with embodiments.
Figure 16A:
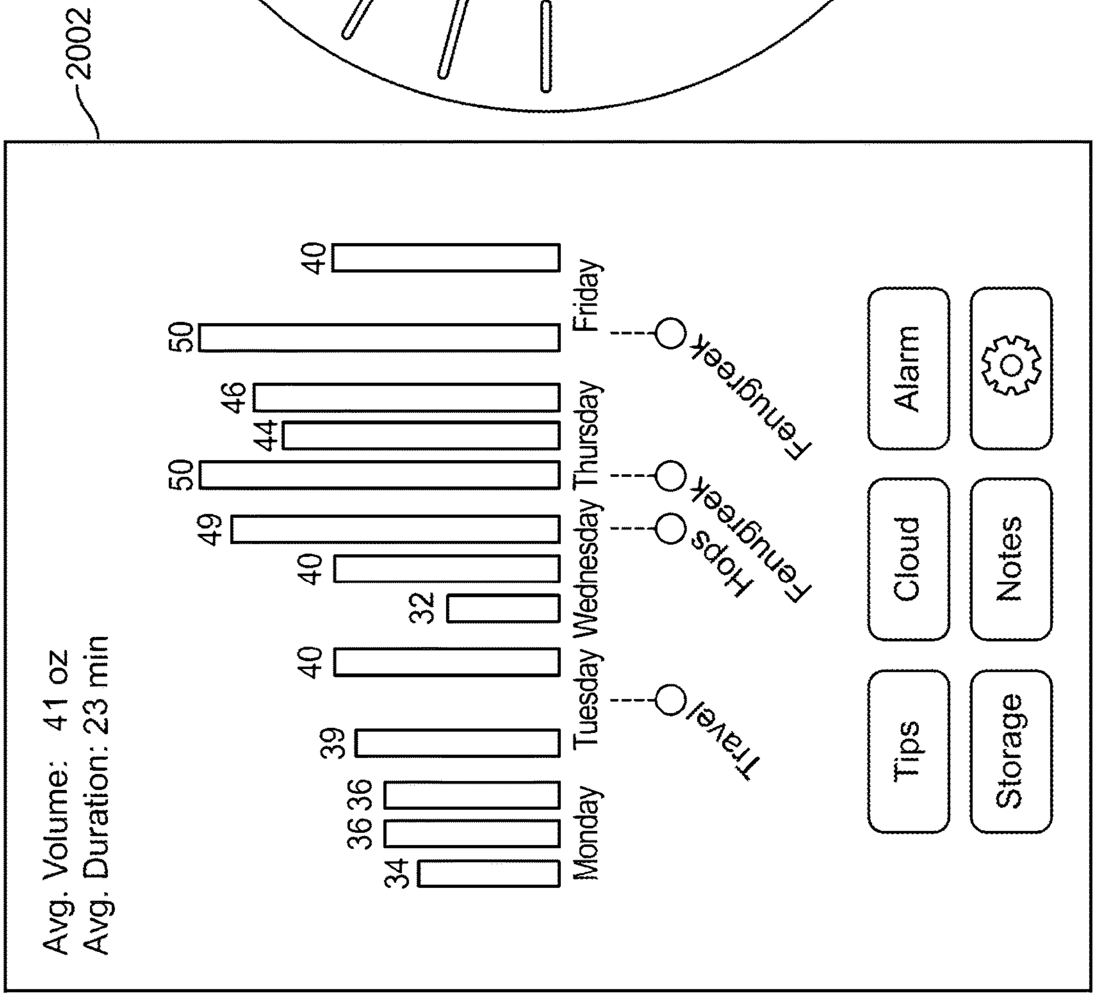

FIGS. 16A-16B illustrate other exemplary displays which may be used in a milk expression system. For example, FIG. 16A is an exemplary display 2002 on any of the computing devices disclosed herein and operably coupled with any of the pump units described herein. The display may indicate an average volume of milk expressed over any time period, along with an average duration of the expression session during that same time period. Graphics may be used (e.g. bar chart, pie chart, x-y plot, etc.) to show volume expressed during individual sessions over the course of several days, here Monday through Friday. The display may allow a user to annotate the display so that missed sessions may be accounted for, for example if a session is omitted due to traveling, the display may show travel during that time period. Other annotations may also be made, such as when certain foods or nutritional supplements are taken, here hops or fenugreek. This allows the user to recall when expressed milk samples were obtained relative to the consumption of the food or nutritional supplements. The display may have other functional buttons such as for obtaining tips, accessing the cloud, setting an alarm, making notes, storing data, or establishing system preferences. FIG. 16B illustrates another exemplary display 2004 of the computing device. The display 2004 is similar to a dashboard style gauge and indicates the volume of fluid expressed and collected and the time. Other information may also be displayed.

The various techniques described herein may be partially or fully implemented using code that is storable upon storage media and computer readable media, and executable by one or more processors of a computer system. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, solid state drives (SSD) or other solid state storage devices, or any other medium which can be used to store the desired information and which can be accessed by the a system device. Based on the disclosure and teachings provided herein, a person of ordinary skill in the art will appreciate other ways and/or methods to implement the various embodiments.

It shall be understood that different aspects of the invention can be appreciated individually, collectively, or in combination with each other. Suitable elements or features of any of the embodiments described herein can be combined or substituted with elements or features of any other embodiment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for containing and measuring breast milk, the system comprising: a breast pump including a breast interface that is configured to seal with a breast; a sensing reservoir for containing and measuring breast milk, wherein the sensing reservoir comprises a fluid sensing unit coupled to the reservoir, the fluid sensing unit extending below where the breast interface seals with the breast and more than half a height of the reservoir and including an extension portion that extends below a bottom of the reservoir, the extension portion connected to and in electronic communication with a processing unit, the fluid sensing unit generates measurement data indicative of a volume of the breast milk of a user contained in the reservoir; and a computing device in communication with the reservoir, the computing device receives the measurement data of the user and includes hardware for milk production quantification.

2. The system of claim 1, wherein the sensing reservoir further comprises a communication module, and the computing device communicates with the sensing reservoir via the communication module.

3. The system of claim 1, wherein the sensing reservoir further comprises one or more reservoir sensors configured to measure one or more of a position, orientation, or motion of the sensing reservoir.

4. The system of claim 1, wherein the processing unit has instructions stored thereon for performing an analysis of the measurement data.

5. The system of claim 1, wherein the computing device comprises a user interface configured to display the measurement data to a user.

6. The system of claim 1, further comprising a remote server in communication with the reservoir or the computing device, the remote server configured to perform one or more of analysis of the measurement data and storage of the measurement data.

7. A method of measuring a fluid contained in a reservoir, the method comprising: providing a breast pump including a breast interface that is configured to seal with a breast and a sensing reservoir for containing and measuring a fluid of a user, the sensing reservoir comprising a fluid sensing unit coupled to a reservoir, the fluid sensing unit extending below where the breast interface seals with the breast and more than half a height of the reservoir and including an extension portion that extends below a bottom of the reservoir, the extension portion connected to and in electronic communication with a processing unit; performing a system check to ensure that the sensing reservoir is functioning properly; generating measurement data using the fluid sensing unit, the measurement data indicative of a volume of the fluid contained in the reservoir; analyzing the measurement data to determine the volume of the fluid contained in the reservoir; and providing a computing device in communication with the sensing reservoir, the computing device receives the measurement data and includes hardware for milk production quantification.

8. The method of claim 7, wherein performing the system check comprises taking one or more baseline measurements using the fluid sensing unit.

9. The method of claim 7, wherein performing the system check comprises confirming that the fluid sensing unit is in communication with a processing unit of the sensing reservoir.

10. The method of claim 7, wherein the sensing reservoir comprises one or more reservoir sensors, and wherein performing the system check comprises measuring one or more of a position, orientation, or motion of the sensing reservoir with the one or more reservoir sensors.

11. The method of claim 10, further comprising determining whether the sensing reservoir is in an inactive state based on the one or more of a position, orientation or motion of the sensing reservoir.

12. The method of claim 10, further comprising determining whether the sensing reservoir is undergoing excessive motion based on the one or more of a position, orientation or motion of the sensing reservoir.

13. The method of claim 7, wherein the sensing reservoir comprises one or more reservoir sensors, and wherein generating measurement data further comprises measuring one or more of a position, orientation, or motion of the sensing reservoir with the one or more reservoir sensors, thereby determining an operating state of the sensing reservoir.

14. The method of claim 13, wherein the operating state of the sensing reservoir comprises a filling state or a draining state.

15. The method of claim 13, wherein the one or more of a position, orientation, or motion of the sensing reservoir comprises one or more of a vertical offset or a rotational offset of the sensing reservoir, and wherein the method further comprises determining whether the sensing reservoir is in an acceptable orientation for generating the measurement data using the fluid sensing unit, based on the one or more of the vertical offset or the rotational offset of the sensing reservoir.

16. The method of claim 7, wherein the fluid sensing unit comprises one or more capacitive sensors, and generating measurement data comprises measuring a capacitance of each of the one or more capacitive sensors, the measured capacitance indicative of a level of fluid at each of the one or more capacitive sensors.

17. The method of claim 7, wherein the fluid sensing unit comprises a plurality of fluid sensors, and analyzing the measurement data comprises determining a level of fluid at each of the plurality of fluid sensors, thereby determining a tilt of the sensing reservoir.

18. The method of claim 7, wherein analyzing the measurement data comprises calculating a volume of fluid contained in the sensing reservoir based on the measurement data generated by the fluid sensing unit and measurement data generated by one or more reservoir sensors configured to measure one or more of a position, orientation, or motion of the sensing reservoir.

19. The method of claim 7, wherein the sensing reservoir further comprises one or more proximity sensors configured to detect one or more proximity triggers disposed within a predetermined distance from the one or more proximity sensors, and wherein the method further comprises generating measurement data using the one or more proximity sensors to determine whether the sensing reservoir is coupled to a component comprising the one or more proximity triggers.

20. The method of claim 19, further comprising setting the sensing reservoir in a standby state in response to a determination that the sensing reservoir is not coupled to the component, and setting the sensing reservoir in a measurement state in response to a determination that the sensing reservoir is coupled to the component, wherein steps of performing the system check, generating the measurement data using the fluid sensing unit, and analyzing the measurement data are performed when the sensing reservoir is set in the measurement state.

21. The method of claim 7, further comprising transmitting the measurement data generated using the fluid sensing unit or the volume of the fluid contained in the reservoir to the computing device in communication with the sensing reservoir.

* * * * *